(12) United States Patent
Lorsbach et al.

(10) Patent No.: US 7,754,724 B2
(45) Date of Patent: Jul. 13, 2010

(54) N-SUBSTITUTED PIPERAZINES

(75) Inventors: Beth Anne Lorsbach, Indianapolis, IN (US); James Melvin Ruiz, Zionsville, IN (US); Thomas Clarence Sparks, Greenfield, IN (US); Michael Thomas Sullenberger, Westfield, IN (US); Irene Mae Morrison, Souix Falls, SD (US); Jeffery Dale Webster, New Palestine, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1048 days.

(21) Appl. No.: 11/479,772

(22) Filed: Jun. 30, 2006

(65) Prior Publication Data

US 2007/0004750 A1    Jan. 4, 2007

Related U.S. Application Data

(60) Provisional application No. 60/695,364, filed on Jun. 30, 2005.

(51) Int. Cl.
*A61K 31/497* (2006.01)
*A61K 31/4965* (2006.01)
*C07D 401/02* (2006.01)
*C07D 403/02* (2006.01)
*C07D 295/02* (2006.01)
*C07D 405/02* (2006.01)

(52) U.S. Cl. .............. 514/253.12; 514/254.01; 514/255.01; 544/360; 544/373; 544/377; 544/386; 544/387

(58) Field of Classification Search ............... 544/360, 544/373, 386, 387, 377; 514/253.12, 254.01, 514/255.01
See application file for complete search history.

(56) References Cited

U.S. PATENT DOCUMENTS 5,981,500 A * 11/1999 Bishop et al. ............ 514/30

OTHER PUBLICATIONS

Ainley et al., Chemical Constitution and Insecticidal Action II, Biochemical Journal (1948), 43; 468-474.*

* cited by examiner

*Primary Examiner*—James O Wilson
*Assistant Examiner*—Ebenezer Sackey
(74) *Attorney, Agent, or Firm*—Carl D. Corvin; Lynn Zettler

(57) ABSTRACT

Novel N-alkyl substituted piperazines have been discovered, which are useful as insecticides or fungicides. Such compounds are of Formula (I)

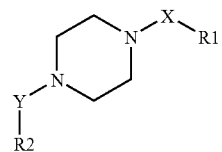

wherein X, Y, R1 and R2 are as defined herein.

6 Claims, No Drawings

N-SUBSTITUTED PIPERAZINES

This application claims the benefit of U.S. Provisional Application No. 60/695,364, filed on Jun. 30, 2005. The present invention relates to novel N-alkyl substituted piperazines and their use as fungicides and insecticides.

BACKGROUND OF THE INVENTION

Various piperazine derivatives have been disclosed in references such as WO 2004/060865, WO 97/26252, WO 01/46166, JP8-26995, JP63-141966, U.S. 2003/0044845, U.S. Pat. Nos. 6,011,035 and 6,387,897. However, these references do not disclose the piperazine derivatives of the present invention.

Additionally, there continues to be a need for additional insecticidal and fungicidal compounds, due to the continual development of resistance to the insecticides and fungicides currently used in the field. For example, there are at least 400 species of arthropods which are resistant to one or more insecticides. Therefore, the need continues to develop new insecticides and fungicides, and particularly for compounds that have new or atypical modes of action.

SUMMARY OF THE INVENTION

The present invention relates to compounds of Formula (I)

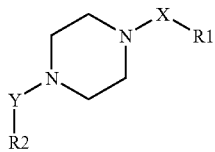

wherein

X and Y are each independently selected from the group consisting of a direct bond, alkyl, carbonyl, carbonylalkyl, carbonylalkylether, carboxylalkyl, alkylcarbonyl, alkylcarboxyl, and alkylether;

with the proviso that both X and Y cannot be a direct bond; and when either X or Y is a direct bond, then the R1 or R2 associated with that bond is not phenyl or optionally substituted phenyl; and R1 and R2 are each independently selected from the group consisting of:

alkyl;

aryl, optionally substituted with cyano, alkoxy, halogen, alkylhalo, alkoxyhalo, carboxylalkyl, carbonylalkyl, benzyloxy, nitro, benzoyl, phenyl, carboxamido, or heteroaryl;

heteroaryl, optionally substituted with aryl, heteroaryl, alkyl, halogen, alkylhalo, alkoxy, cycloalkyl or cyano;

cycloalkyl, optionally substituted with alkyl or halogen; and a heterocyclic ring, optionally substituted with alkyl.

The present invention also relates to insecticidal or fungicidal compositions thereof and methods of use.

DETAILED DESCRIPTION OF THE INVENTION

The present invention relates to the compounds of Formula (I), compositions thereof and their use as insecticides and fungicides, in accordance with the definitions herein. In relation to the definitions hereafter, R is an alkyl group; X refers to a halogen atom, and the symbol '*' denotes the point of attachment.

The term "alkoxy" refers to an alkyl group, attached through an oxygen atom, e.g. *—OR.

The term "alkoxyhalo" refers to an alkoxy group which is substituted with one or more halogens (*—O—R—$X_n$).

The term "alkyl" (including derivative terms such as alkoxy) as used herein includes straight and branched chains containing from 1 to 6 carbon atoms. Thus, typical alkyl groups are methyl, ethyl, 1-methylethyl, propyl, and 1,1-dimethylethyl, and the like.

The term "alkylcarbonyl" refers to an alkyl group attached to a carbonyl (*—R—C(O)—).

The term "alkylcarboxyl" refers to an alkyl group attached to a carboxyl group (*—R—C(O)—O—).

The term "alkylether" refers to an alkyl group attached to an oxygen (*—R—O—).

The term "alkylhalo" refers to an alkyl group which is substituted with one or more halogens (*—R—$X_n$).

The term "aryl" refers to a mono or bicyclic aromatic ring, such as phenyl or naphthalene.

The term "benzodioxane" refers to a 10 membered, fused, bicyclic aromatic ring containing two oxygen atoms in the para position of the second, 6-membered, non-aromatic ring, i.e. a benzene ring fused to a dioxane ring.

The term "benzodioxole" refers to a 9 membered, fused, bicyclic aromatic ring containing two non adjacent oxygen atoms in the second, five-membered, non-aromatic ring, i.e. a benzene ring fused to a dioxole ring.

The term "benzothiophene" refers to a 9 membered, fused, bicyclic aromatic ring containing one sulfur atom, i.e. a benzene ring fused to a thiophene ring.

The term "benzoyl" refers to a carbonyl group attached to a phenyl group (*—C(O)-phenyl).

The term "benzyloxy" refers to a benzyl group attached to an oxygen atom (*—O—$CH_2$-phenyl).

The term "carbonyl" refers to a carbon atom double bonded to an oxygen atom (*—C(O)—).

The term "carbonylalkyl" refers to a carbonyl group attached to an alkyl group (*—C(O)—R—).

The term "carbonylalkylether" refers to a carbonyl group attached to an alkylether group (*—C(O)—R—O—).

The term "carboxamido" refers to a carbonyl group attached to an amino group (*—C(O)—$NH_2$).

The term "carboxylalkyl" refers to a carboxyl group attached to an alkyl group (*—C(O)—O—R—).

The term "cyano" refers to a carbon atom triple bonded to a nitrogen atom (*—C≡N).

The term "cycloalkyl" refers to a saturated $C_3$-$C_6$ membered ring, such as cyclobutane, cyclopropane, cyclohexane and the like.

The term "halogen" or "halo" refers to the atoms fluorine, chlorine, bromine, and iodine.

The term "heteroaryl" refers to a 5 or 6 membered unsaturated ring containing one, two or three heteroatoms, preferably one or two heteroatoms independently selected from oxygen, nitrogen and sulfur; or to a bicyclic unsaturated ring system containing up to 11 atoms including one, two or three heteroatoms selected from oxygen, nitrogen and sulfur. Examples of heteroaryl ringss include, but are not limited to, 2-, 3- or 4-pyridine, pyrazine, pyrazole, 2-, 4-, or 5-pyrimidine, 2- or 3-thiophene, 2- or 3-furan, oxazole, quinoline, benzofuran, benzopyronye, benzothiophene, thiophenepyrazoline, thiadiazole, benzodioxane, benzodioxole, indole, pyridazine, triazole, imidazole, pyrrole, isoxazole, thiazole, isothiazole, oxadiazole, thiadiazole isoquinoline and the like.

The ring may be attached at any position so long as the laws of chemical valency and stereochemistry are observed.

The term "heterocyclic" refers to a 3 to 5 membered, saturated ring containing 1-3 heteroatoms selected from oxygen, nitrogen or sulfur; such as oxirane, pyrrolidine, morpholine rings and the like. The ring may be attached at any position so long as the laws of chemical valency and stereochemistry are observed.

The term "nitro" refers to a nitrogen atom bonded to two oxygen atoms, (*—$NO_2$).

The term "oxazole" refers to a 5 membered, aromatic ring containing one oxygen atom and one nitrogen atom, non-adjacent to each other, i.e. an oxazole ring.

The term "oxirane" refers to a 3 membered ring containing oxygen and carbon, i.e.

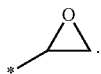

The term "pyrazine" refers to a 6 membered, aromatic ring containing 2 nitrogen atoms, wherein the N's are in the para position.

The term "pyrazole" refers to a 5 membered, aromatic ring containing 2 nitrogen atoms, wherein the N's are adjacent to one another.

The term "thiadiazole" refers to a 5 membered, aromatic ring containing two nitrogen atoms and a sulfur atom.

The term "thiophenepyrazoline" refers to a 8 membered, fused, bicyclic aromatic ring containing one sulfur atom, and two nitrogen atoms, wherein the sulfur atom is part of a thiophene ring and the nitrogen atoms are part of a pyrazoline ring fused therewith.

In one embodiment of the present invention X and Y are each independently selected from the group consisting of a direct bond, alkyl, and carbonyl;

with the proviso that both X and Y cannot be a direct bond; and when either X or Y is a direct bond, then the R1 or R2 associated with that bond is not phenyl or optionally substituted phenyl; and R1 and R2 are each independently selected from the group consisting of:

aryl, optionally substituted with cyano, alkoxy, halogen, alkylhalo, alkoxyhalo, carboxylalkyl, carbonylalkyl, benzyloxy, nitro, benzoyl, phenyl, carboxamido, or heteroaryl; and heteroaryl, optionally substituted with aryl, heteroaryl, alkyl, halogen, alkylhalo, alkoxy, cycloalkyl or cyano.

The compounds of the present invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of the present invention can be prepared by known methods in the art as outlined in the examples of the present specification.

Another aspect of the present invention relates to an insecticidal or fungicidal composition comprising a compound of Formula (I) and a phytologically-acceptable inert carrier. The compositions are typically either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides, acaricides and fungicides are generally applied in the form of a dispersion of the active ingredient in a liquid carrier. It is conventional to refer to application rates in terms of the concentration of active ingredient in the carrier. The most widely used carrier is water.

The compounds of the present invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0% by volume, based on a spray-volume of water, preferably 0.05 to 0.5 volume %. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

Another aspect of the present invention relates to a method for inhibiting an insect which comprises applying to a locus of the insect an insect-inhibiting amount of a compound of Formula (I).

The "locus" of insects is a term used herein to refer to the environment in which the insects live or where their eggs are present, including the air surrounding them, the food they eat, or objects which they contact. For example, insects which eat or contact edible or ornamental plants can be controlled by applying the active compound to plant parts such as the seed, seedling, or cutting which is planted, the leaves, stems, fruits, grain, or roots, or to the soil in which the roots are growing. It is contemplated that the compounds might also be useful to protect textiles, paper, stored grain, seeds, domesticated animals, buildings or human beings by applying an active compound to or near such objects. The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The terms "insect-inactivating amount" are used to describe the amount, which is sufficient to cause a measurable reduction in the treated insect population. Generally an amount in the range from about 1 to about 1000 ppm by weight active compound is used.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Another embodiment of the present invention is a method for the control or prevention of fungal attack. This method comprises applying to the soil, plant, roots, foliage, seed or locus of the fungus, or to a locus in which the infestation is to be prevented (for example applying to cereal or grape plants), a fungicidal effective amount of one or more of the compounds. The compounds are suitable for treatment of various plants at fungicidal levels, while exhibiting low phytotoxicity. The compounds are useful both in a protectant and/or an eradicant fashion.

The compounds have been found to have significant fungicidal effect particularly for agricultural use. Many of the compounds are particularly effective for use with agricultural crops and horticultural plants. It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Additionally, the compounds of the present invention (Formula I) are often applied in conjunction with one or more other insecticides or fungicides to obtain control of a wider variety of pests and diseases. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I, and the pesticidal compound in the combination can generally be present in a weight ratio of from 1:100 to 100:1.

When used in conjunction with other insecticides or fungicides, the presently claimed compounds can be formulated with the other insecticides or fungicides, tank mixed with the other insecticides or fungicides, or applied sequentially with the other insecticides or fungicides.

Some of the insecticides that can be employed beneficially in combination with the compounds of the present invention include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, niethomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zetacypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cis-methrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate and any combinations thereof.

Some of the fungicides that can be employed beneficially in combination with the compounds of the present invention include, but are not limited to: enestrobin, antimycin, quinoxyfen, SYP-048, IK-1140, NC-224, 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenyl-itaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

EXAMPLES

Throughout the present specification, all temperatures are given in degrees Celsius, and all percentages are weight percentages unless otherwise stated. The following examples are representative of the embodiments of the present invention and should not be read as limiting.

The compounds of the present invention may be synthesized by methods that are individually known to those skilled in the art.

The compounds of Formula I wherein R1, R2, X, Y, are previously defined can be prepared by the methods illustrated in the following schemes.

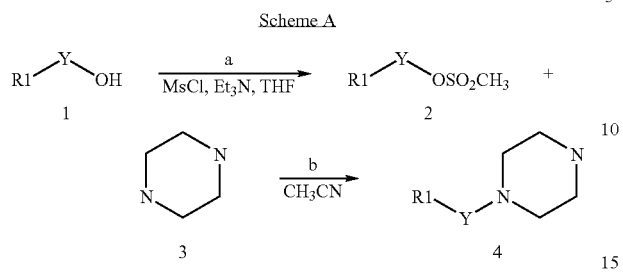

Scheme A

In step a, of scheme A, alcohol 1 is treated with methan sulfonyl chloride and triethylamine (Et₃N) at 0° C. to yield mesylate 2, which undergoes a nucleophilic displacement with piperazine in step b, to deliver compound 4. The preferred solvent for the nucleophilic displacement is acetonitrile (CH₃CN) and elevated temperatures are required to drive the reaction to completion. Commercial mono-substituted piperazines were used directly in schemes B and C when available.

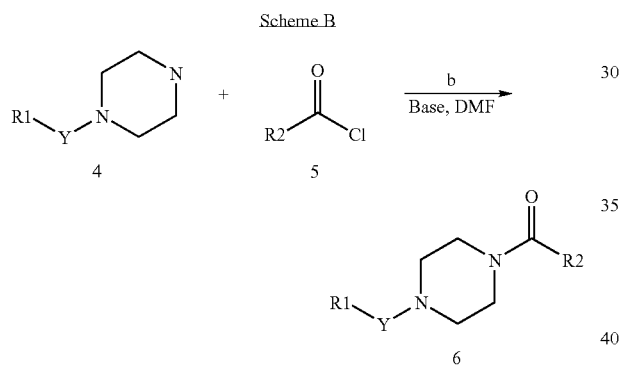

Scheme B

As depicted in step a, a substituted piperazine, 4, is reacted with an acid chloride 5 to yield the appropriately acyl piperazine 6. The acylation is performed under basic conditions to neutralize the hydrochloric acid (HCl) formed during the reaction; examples of typical bases are diisopropylamine (DIEA) and Et₃N.

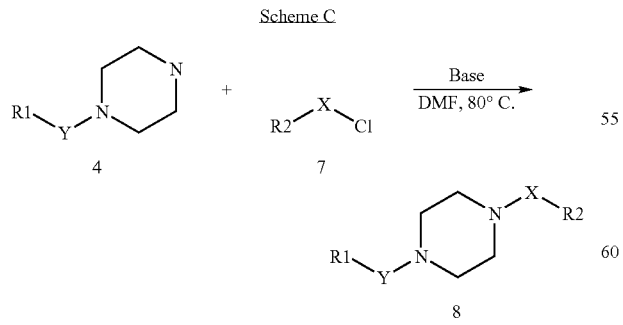

Scheme C

As depicted in Scheme C, a substituted piperazine, 4, is reacted with chloro derivative 7 (note bromides can also be used) and heated at 80° C. in dimethylformamide (DMF) to give the appropriately substituted piperazine 8. The reaction is performed under basic conditions to neutralize the HCl formed during the reaction; examples of typical bases are DIEA and Et₃N.

Alternatively, t-butylcarbamate (BOC) protected piperazine can be utilized as illustrated in schemes D and E. In step a, of scheme D, BOC protected piperazine is N-acylated with an acid chloride utilizing similar reactions previously described to yield compound 10. The BOC group is removed with trifluoroacetic acid (TFA) in methylene chloride (CH₂Cl₂) and the free base 11, is N-alkylated, again utilizing reaction conditions described earlier, to yield derivatives of 6.

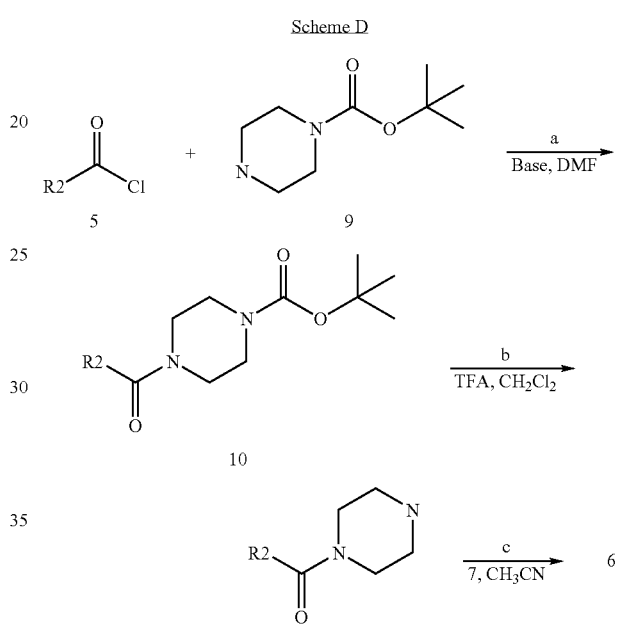

Scheme D

The N-acylation and N-alkylation steps in scheme D can be reversed as shown in scheme E to deliver derivatives of 6.

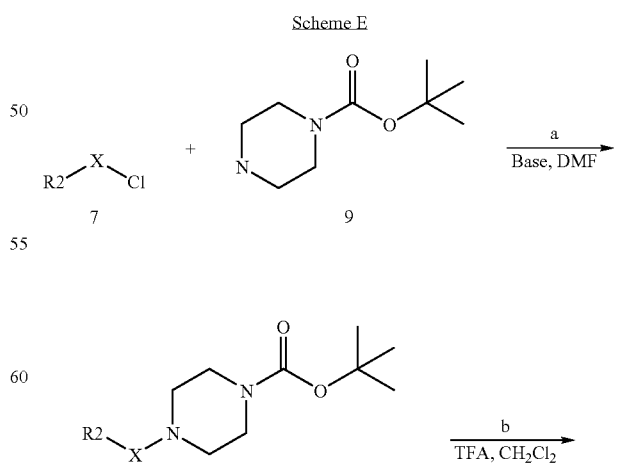

Scheme E

-continued

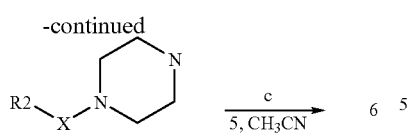

The following examples further illustrate the present invention, but, are not to be construed as in any way limiting its scope.

Example I

1-Benzyl-4-[(3,5-dimethylisoxazol-4-yl)carbonyl] piperazine (14)

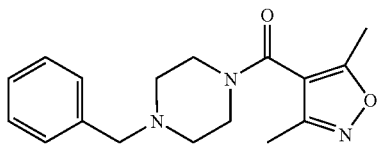

To a 2-dram screw-cap vial was added polymer-supported diisopropylethylamine (PS-DIEA, 54 mg, 0.2 mmol based on 3.68 mmol/g loading of resin) and DMF (2 mL). The vials were placed in an orbital shaker allowed to shake for 15 min. 1-Benzylpiperazine (35 mg, 0.2 mmol) was dissolved in DMF (100 μL) and transferred by pipette to the vial. 3,5-Dimethylisoxazole-4-carbonyl chloride (32 mg, 0.2 mmol), was dissolve in DMF (100 μL) and transferred to the vial. The vial was capped and allowed to shake at room temperature (RT) for 12 h. The reaction mixture filtered and solvent evaporated to give the desired acylated piperazine. MS ELS+300.

Example II 1-(2-methyoxybenzoyl)-4-{2-[2-trifluoromehtyl) phenyl]ethyl}piperazine (15)

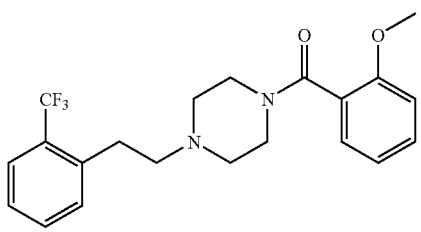

1-[2-(Trifluoromethyl)phenethyl]piperazine (200 mg, 0.60 mmol), o-anisyl chloride (100 mg, 0.59 mmol), and Et₃N (253 μL, 1.81 mmol) were dissolved in DMF (10 mL) and stirred at ambient temperature for 12 h. The reaction mixture was extracted with diethylether (Et₂O) and the combined organic layers washed with brine, dried over anhydrous sodium sulfate (Na₂SO₄) and evaporated to give an amber oil (120 mg, 51%). 1H NMR (CDCl₃) δ: 2.4-2.7 (m, 6H), 2.9-3.0 (t, 2H), 3.2-3.35 (m, 2H), 3.8-3.95 (m, 5H), 6.89-7.01 (m, 2H), 7.22-7.37 (m, 4H), 7.43-7.49 (t, 1H), 7.59-7.62 (d, 1H). MS ELS+393.

Example III

1-[(6-chloro-1,3-benzodioxol-5-yl)methyl]-4-(2-phenoxyethyl) piperazine (16)

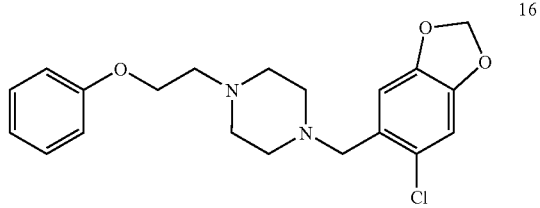

1-[2-(phenoxy)-ethyl]piperazine (200 mg, 0.974 mmol), 6-chloropiperonyl chloride (200 mg, 0.974 mmol), and Et3N (415 μL, 3 mmol) were combined in tetrahydrofuran (THF 20 mL). The reaction mixture was heated at 60° C. for 12 h. The reaction mixture was cooled and extracted with ethyl acetate (EtOAc). The combined organic layers were washed with brine, dried over anhydrous Na₂SO₄ and evaporated. The crude residue was chromatographed on silica (20% EtOAc/Hexanes) and the product fractions were collected and evaporated to an amber solid (186 mg, 51%). 1H NMR (CDCl₃) δ: 2.5-2.7 (m, 8H), 2.8 (t, 2H), 3.5 (s, 2H), 4.1 (t, 2H), 5.9 (s, 2H), 6.81 (s, 1H), 6.9-6.94 (m, 3H), 6.96-6.98 (m, 1H), 7.26-7.3 (m, 1H). MS ELS+376. CHN: calc., 64.08, 6.18, 7.47; found, 63.87, 6.12, 7.44. mp: 72-76° C.

Example IV

3-{[4-(2-phenylethyl)piperazin-1-yl] methyl}benzonitrile (17)

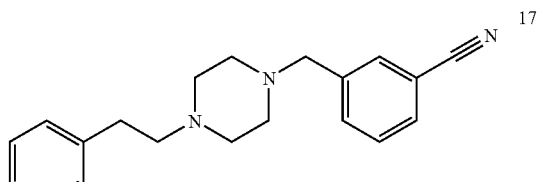

To a 2-dram screw-cap vial was added PS-DIEA (54 mg, 0.2 mmol) and DMF (2 mL). The vials were placed in an orbital shaker allowed to shake for 15 min. 1-(2-phenylethyl)-piperazine (38 mg, 0.2 mmol was dissolved in DMF (100 μL) and transferred by pipette to the vial. 3-Chloromethylbenzonitrile (30 mg, 0.2 mmol), was dissolve in DMF (100 μL) and transferred to the vial. The vial was capped and heated at 80° C. with shaking for 12 h. The vial was cooled to RT and the reaction mixture filtered and solvent evaporated to give the desired substituted piperazine. MS ELS+306.

Intermediate Compound 2-(2,4-dichlorophenyl)ethyl methanesulfonate (18)

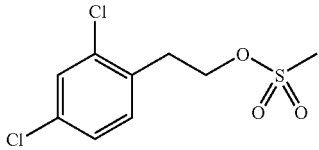

To a stirred mixture of 2,4-dichlorophenethylalcohol (955.0 mg, 5.0 mol) at 0° C. was added Et$_3$N (1.1 mL, 7.5 mmol) and stirred for 5 min. Methane sulfonyl chloride (572.8 mg, 5.0 mmol) was added neat, dropwise by syringe. A precipitate formed and the reaction mixture stirred 30 min. The mixture was filtered, diluted with Et$_2$O (20 mL) and cooled at to 0° C. After 20 min., the mixture was filtered through a pad of silica, dried over anhydrous Na$_2$SO$_4$ and evaporated. The crude residue was co-evaporated with toluene and chloroform (1:1) to give a yellow oil (1.1 g, 80%). The mesylate was used directly in subsequent reactions. 1H NMR (CDCl$_3$) δ 2.9 (s, 3H), 3.18 (t, 2H), 4.42 (t, 2H), 7.22 (d, 2H), 7.41 (t, 1H).

Intermediate Compound 1-[(2-(2,4-dichlorophenyl)ethyl]piperazine (19)

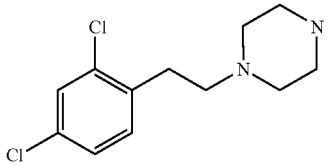

Piperazine (1.9 g, 22 mmol) was stirred in 20 mL CH$_3$CN at 75° C. Compound 19 (1.1 g, 4.1 mmol) was dissolved in CH$_3$CN (2 mL) and added dropwise via syringe. The reaction mixture was heated at 60° C. for 30 min. The mixture was poured over ice and extracted with EtOAC. The combined organic layers were washed with water, dried over anhydrous magnesium sulfate (MgSO$_4$), and evaporated to yield the desired piperazine as a yellow oil (826 mg, 80%). 1H NMR (CDCl$_3$) δ 2.55 (bm, 6H), 2.9 (bm, 6H), 7.19 (d, 2H), 7.36 (t, 1H)

Example V tert-butyl 4-(2-phenylpropanoyl)piperazine-1-carboxylate (20)

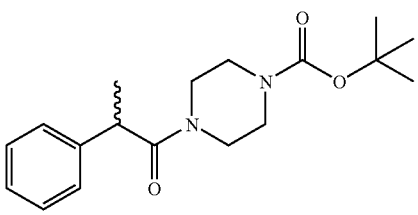

To a stirred mixture of 2-phenyl propionic acid (1.0 g, 6.7 mmol) in 1,2-dichloroethane (15 mL) was added a few drops of DMF and excess thionyl chloride. The resulting mixture was heated at reflux for 2 h, when bubbling ceased the mixture was evaporated to dryness. The crude residue was co-evaporated with toluene and 1,2-dichloroethane. The residue was dissolved in CH$_2$Cl$_2$ and cooled to 0° C. To the stirred solution, BOC-piperazine (1.24 g, 6.7 mmol) and Et$_3$N were added. A white precipitate formed and the reaction was stirred 12 h at RT. Et$_2$O was added and the mixture was washed with water and brine. The ether layer was separated and dried over anhydrous Na$_2$SO$_4$, filtered, and evaporated. The residue was treated with 20% ether/hexanes and the resulting solid filtered. The filtrate was evaporated and the procedure repeated. After drying, there remained a white solid (1.3 g, 62%). 1H NMR (CDCl$_3$) δ: 1.4 (s, 9H), 1.42 (d, 3H), 2.7 (m, 1H), 3.1-3.6 (m, 6H), 3.85 (m, 2H), 7.2-7.4 (m, 5H). [M+Na] 341.

Example VI

1-[(6-chloro-1,3-benzodioxol-5-yl)methyl]-4-(2-phenylpropanoyl)piperazine (21)

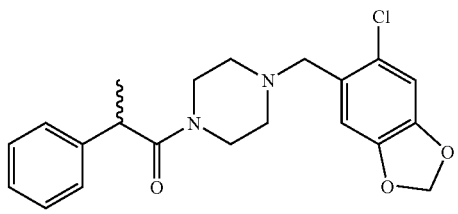

To a stirred mixture of compound 201 (500 mg, 1.57 mmol) in CH$_2$Cl$_2$ was added trifluoroacetic acid TFA (excess). The mixture was stirred 1 h and was evaporated to dryness. The crude residue was dissolved in DMF and 6-chloropiperonyl chloride (321 mg, 1.57 mmol), and Et$_3$N were added. The reaction mixture was stirred at 80° C. for 3 h after which the mixture was poured into water and extracted with Et$_2$O. The combined Et$_2$O layers were washed with water, brine and dried over anhydrous Na$_2$SO$_4$, filtered, and evaporated to give orange oil (500 mg, 83%). 1H NMR (CDCl$_3$) δ: 1.42 (d, 3H), 1.95 (m, 1H), 2.25-2.5 (m, 3H), 3.2-3.8 (bm, 4H), 3.41 (s, 2H), 3.85 (q, 1H), 5.95 (s, 2H), 6.79 (s, 1H), 6.9 (s, 1H), 7.2-7.35 (m, 5H).

Example VII

1-[(6-chloro-1,3-benzodioxol-5-yl)methyl]-4-(2-phenylpropyl)piperazine (22)

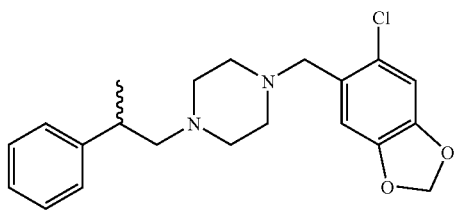

To a stirred mixture of compound 21 (200, mg 0.52 mmol) in THF (7.0 mL) was added lithium aluminum hydride (LAH)

(0.4 mL of 1M in THF). The mixture was refluxed for 1 h. To the cooled mixture was added ice-water to quench unreacted LAH. The mixture was stirred 1 h and extracted with Et$_2$O and the combined organic layers were washed with brine, dried over anhydrous Na$_2$SO$_4$, and evaporated. The crude residue was purified via flash column (20% EtOAc/Hexanes) and the product fractions evaporated to give an orange oil (179.8 mg, 93%). 1H NMR (CDCl$_3$) δ:1.15 (d, 3H), 2.35-2.55 (bm, 10H), 2.9 (m, 1H), 3.5 (s, 2H), 5.98 (s, 2H), 6.8 (s, 1H), 6.95 (s, 1H) 7.18-7.35 (m, 5H). GC-MS: calcd, 372; found, 372.

TABLE 1 lists compounds of the invention prepared according to the procedures described in Scheme A-D as well as illustrated by Examples I-VII.

TABLE 1

| Compound # | Structure | Characterization |
|---|---|---|
| 23 | 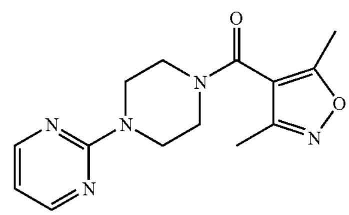 | [M + H]+: 288 |
| 24 | 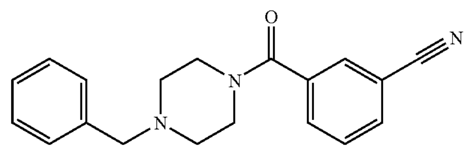 | [M + H]+: 306 |
| 25 | 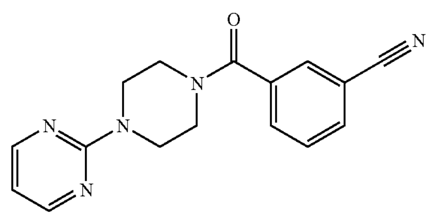 | [M + H]+: 294 |
| 26 | 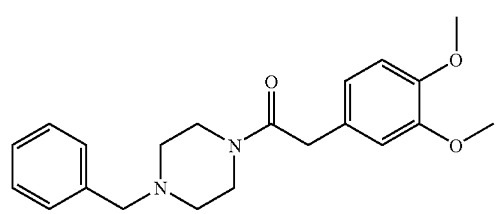 | [M + H]+: 355 |
| 27 | 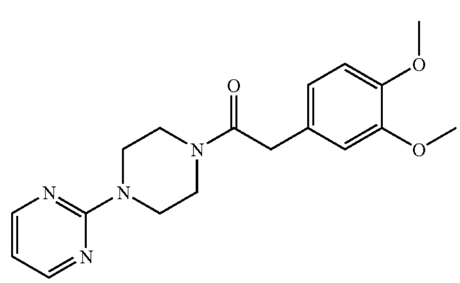 | [M + H]+: 343 |
| 28 | 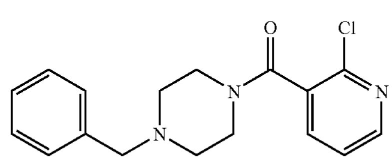 | [M + H]+: 316 |

TABLE 1-continued

| Compound # | Structure | Characterization |
| --- | --- | --- |
| 29 | 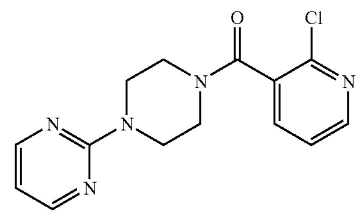 | [M + H]+: 304 |
| 30 | 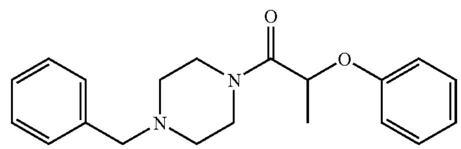 | [M + H]+: 325 |
| 31 | 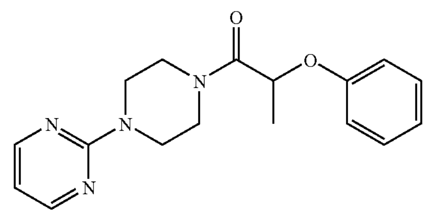 | [M + H]+: 313 |
| 32 | 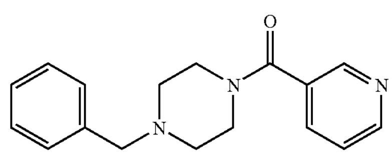 | [M + H]+: 282 |
| 33 | 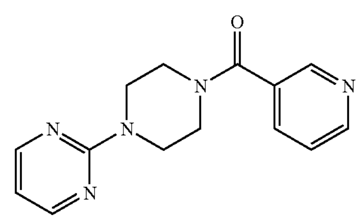 | [M + H]+: 270 |
| 34 | 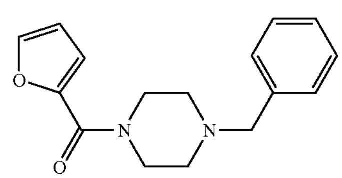 | [M + H]+: 271 |
| 35 | 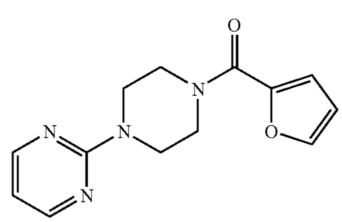 | [M + H]+: 259 |

TABLE 1-continued

| Compound # | Structure | Characterization |
|---|---|---|
| 36 | 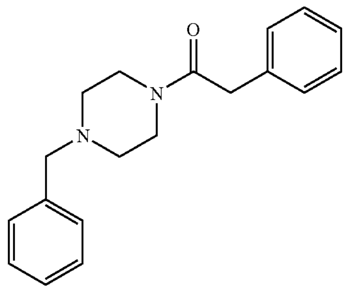 | [M + H]+: 295 |
| 37 | 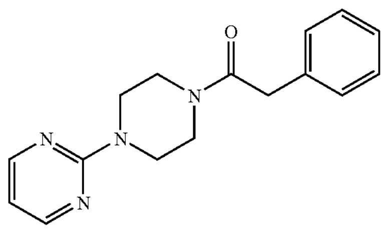 | [M + H]+: 283 |
| 38 | 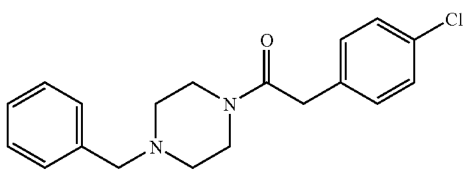 | [M + H]+: 329, 331 |
| 39 | 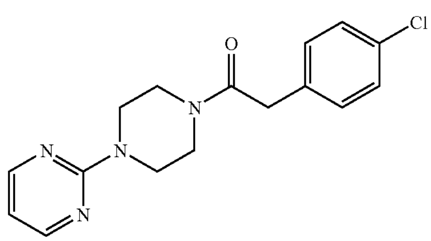 | [M + H]+: 317 |
| 40 | 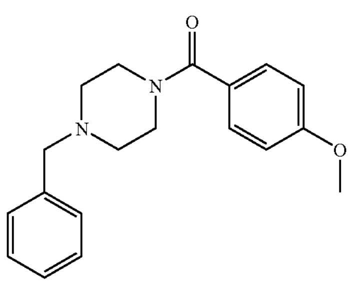 | [M + H]+: 311 |
| 41 | 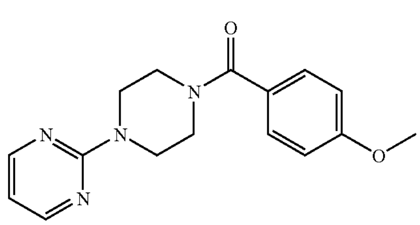 | [M + H]+: 299 |

TABLE 1-continued

| Compound # | Structure | Characterization |
|---|---|---|
| 42 | 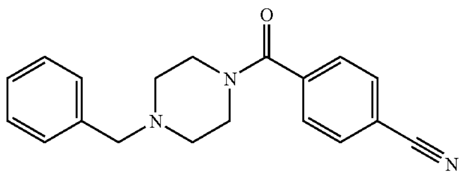 | [M + H]+: 306 |
| 43 | 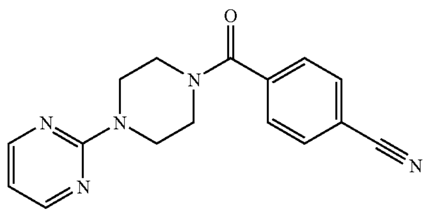 | [M + H]+: 294 |
| 44 | 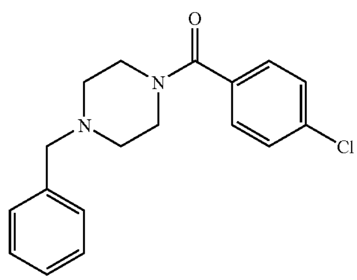 | [M + H]+: 315, 317 |
| 45 | 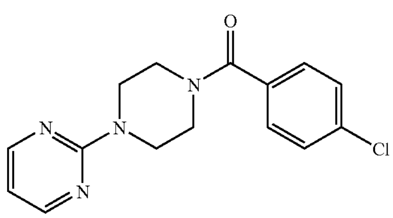 | [M + H]+: 303 |
| 46 | 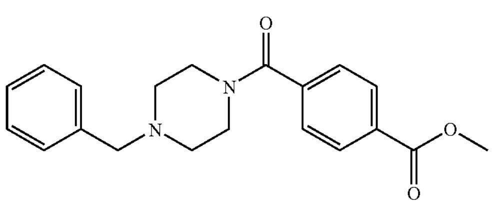 | [M + H]+: 339 |
| 47 | 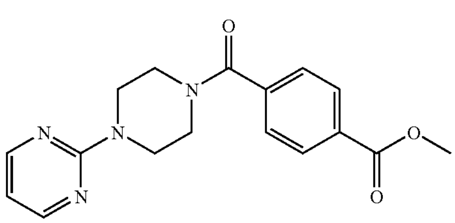 | [M + H]+: 327 |
| 48 | 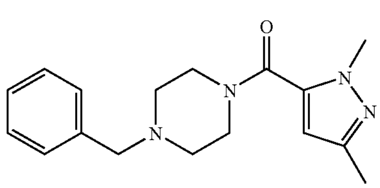 | [M + H]+: 299 |

TABLE 1-continued

| Compound # | Structure | Characterization |
|---|---|---|
| 49 | 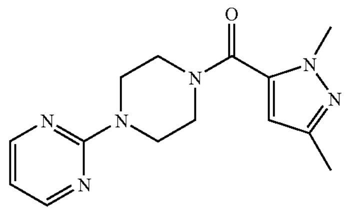 | [M + H]+: 287 |
| 50 | 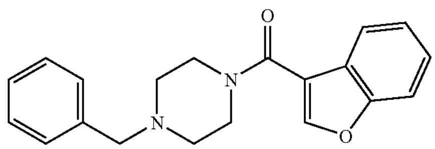 | [M + H]+: 321 |
| 51 | 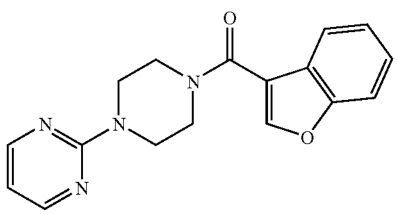 | [M + H]+: 309 |
| 52 | 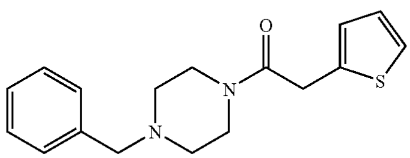 | [M + H]+: 301 |
| 53 | 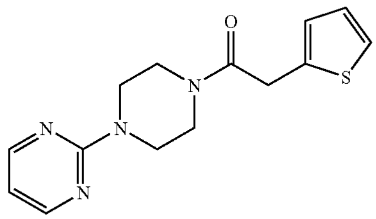 | [M + H]+: 289 |
| 54 | 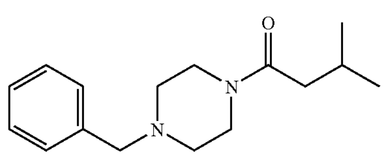 | [M + H]+: 261 |
| 55 | 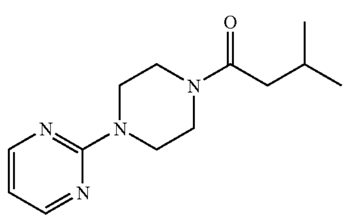 | [M + H]+: 249 |
| 56 | 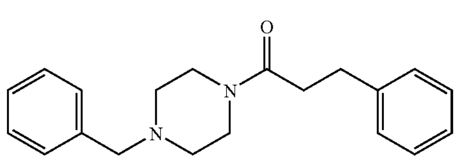 | [M + H]+: 309 |

TABLE 1-continued
| Compound # | Structure | Characterization |
|---|---|---|
| 57 | 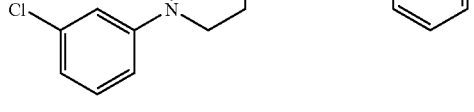 | [M + H]+: 331, 333 |
| 58 | 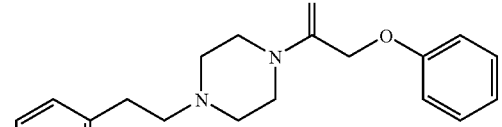 | [M + H]+: 393 |
| 59 | 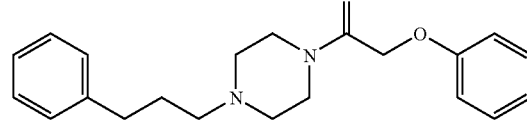 | [M + H]+: 339 |
| 60 | 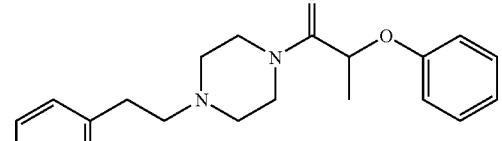 | [M + H]+: 407 |
| 61 | 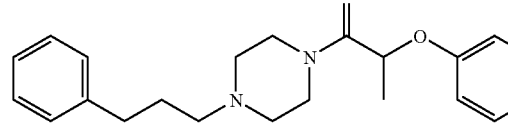 | [M + H]+: 353 |
| 62 | 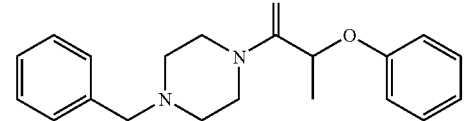 | [M + H]+: 339 |
| 63 | 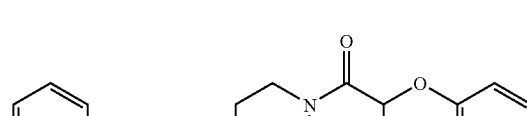 | [M + H]+: 369 |

TABLE 1-continued

| Compound # | Structure | Characterization |
|---|---|---|
| 64 | 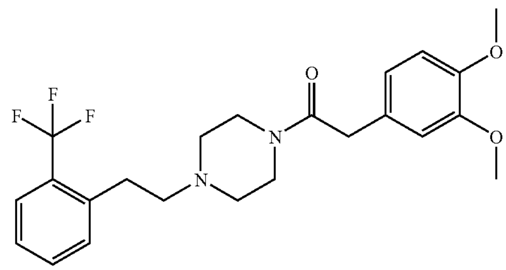 | [M + H]+: 437 |
| 65 | 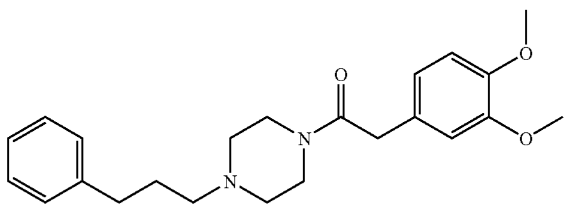 | [M + H]+: 383 |
| 66 | 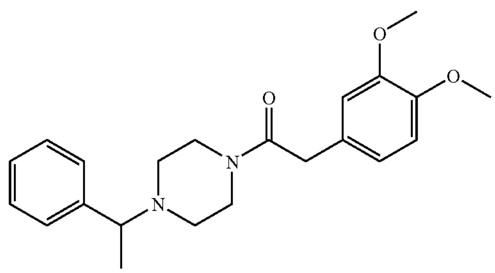 | [M + H]+: 391 |
| 67 | 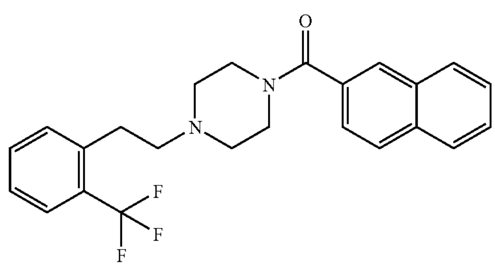 | [M + H]+: 413 |
| 68 | 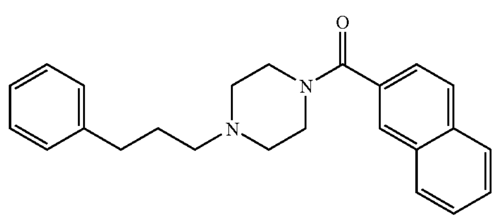 | [M + H]+: 359 |
| 69 | 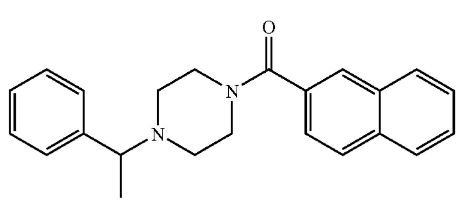 | [M + H]+: 345 |

TABLE 1-continued

| Compound # | Structure | Characterization |
|---|---|---|
| 70 | 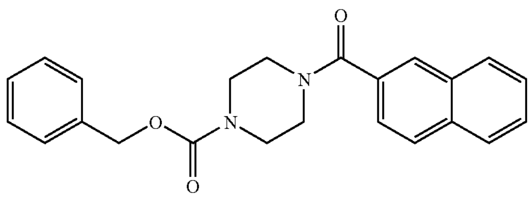 | [M + H]+: 375 |
| 71 | 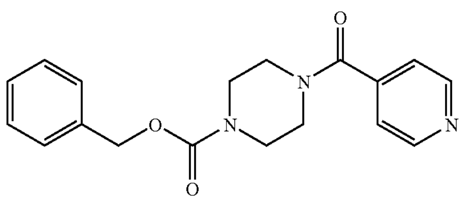 | [M + H]+: 326 |
| 72 | 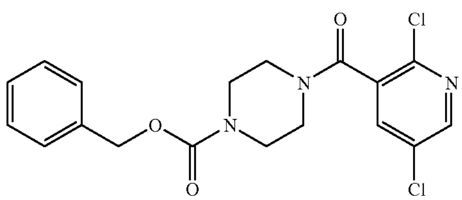 | [M + H]+: 396 |
| 73 | 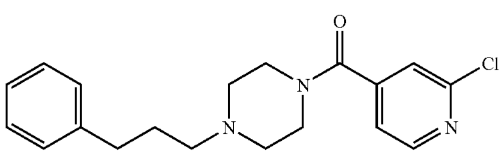 | [M + H]+: 345 |
| 74 | 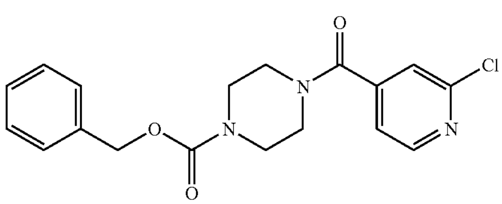 | [M + H]+: 360 |
| 75 | 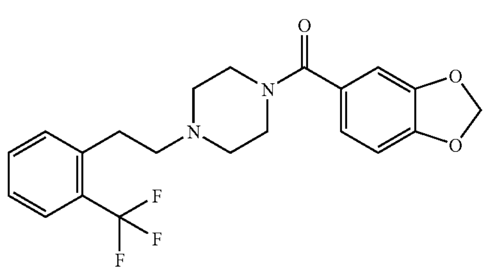 | [M + H]+: 407 |
| 76 | 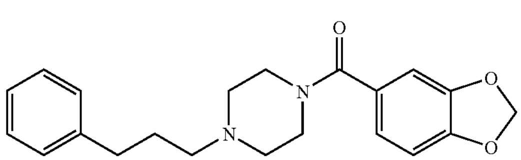 | [M + H]+: 353 |

TABLE 1-continued

| Compound # | Structure | Characterization |
|---|---|---|
| 77 | 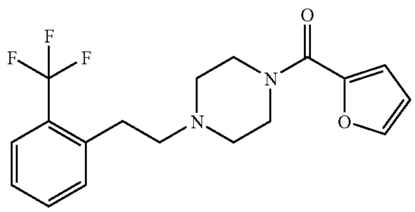 | [M + H]+: 353 |
| 78 | 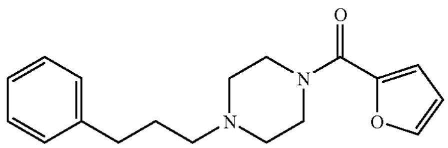 | [M + H]+: 299 |
| 79 | 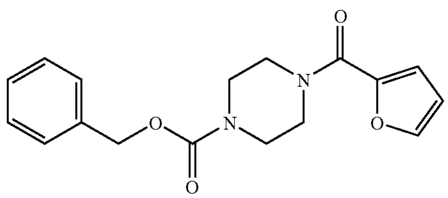 | [M + H]+: 337 |
| 80 | 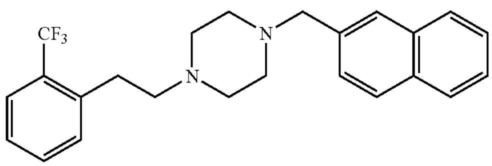 | [M + H]+: 399 |
| 81 | 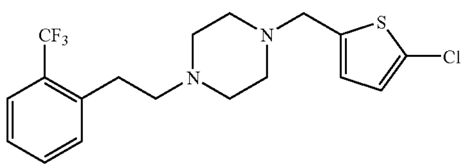 | [M + H]+: 389 |
| 82 | 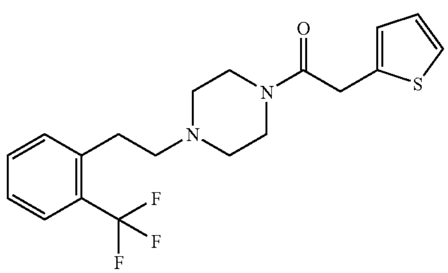 | [M + H]+: 383 |
| 83 | 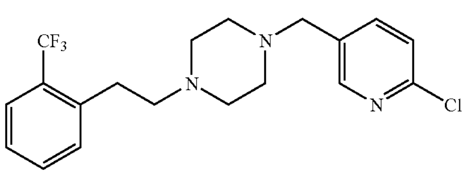 | [M + H]+: 384, 386 |
| 84 | 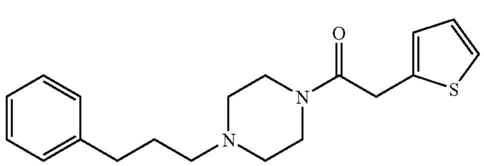 | [M + H]+: 329 |

TABLE 1-continued

| Compound # | Structure | Characterization |
|---|---|---|
| 85 | 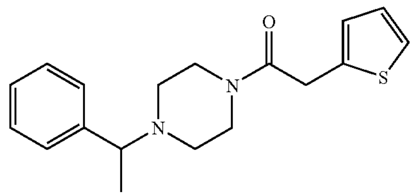 | [M + HI+: 315 |
| 86 | 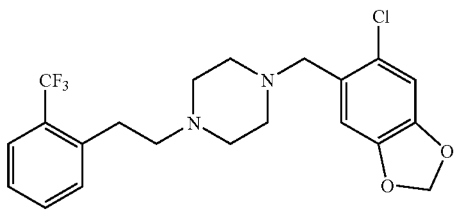 | [M + H]+: 427, 430 |
| 87 | 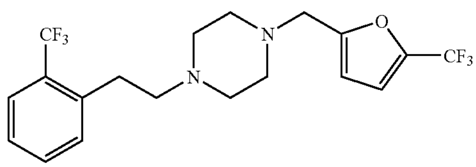 | [M + H]+: 407 |
| 88 | 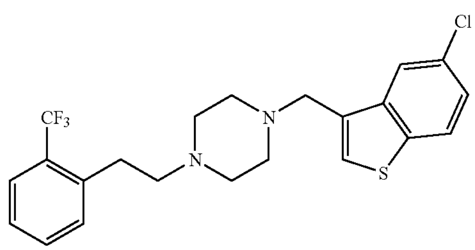 | [M + H]+: 439 |
| 89 | 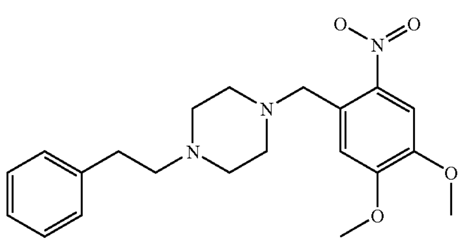 | [M + H]+: 386 |
| 90 | 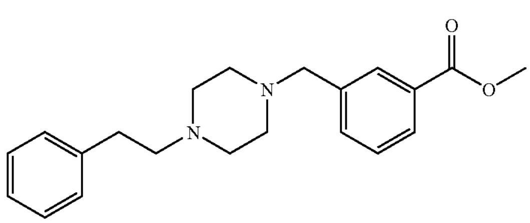 | [M + H]+: 339 |
| 91 | 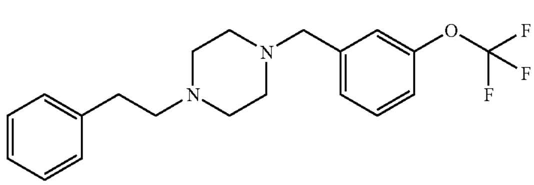 | [M + H]+: 365 |

TABLE 1-continued

| Compound # | Structure | Characterization |
|---|---|---|
| 92 | 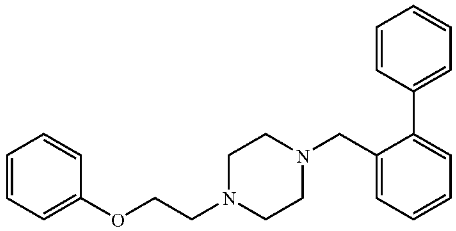 | [M + H]+: 373 |
| 93 | 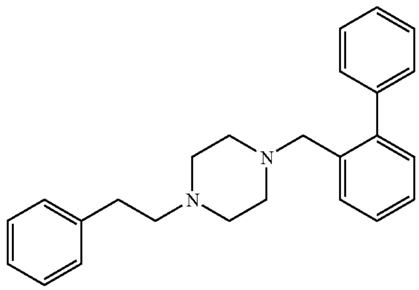 | [M + H]+: 357 |
| 94 | 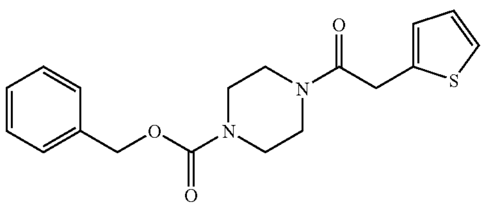 | [M + H]+: 345 |
| 95 | 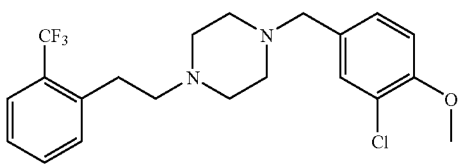 | [M + H]+: 413 |
| 96 | 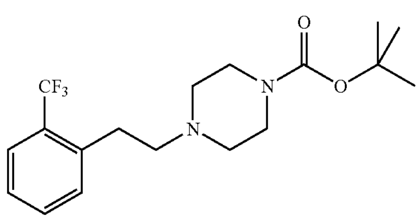 | [GC − MS]: 357 |
| 97 | 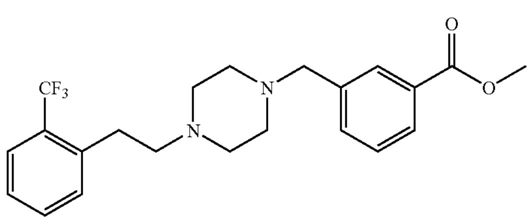 | [M + H]+: 407 |

TABLE 1-continued
| Compound # | Structure | Characterization |
|---|---|---|
| 98 | 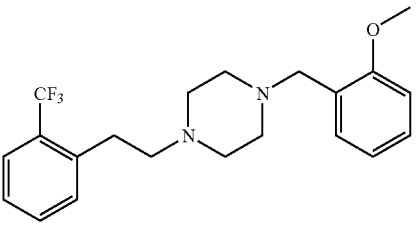 | [M + H]+: 393 |
| 99 | 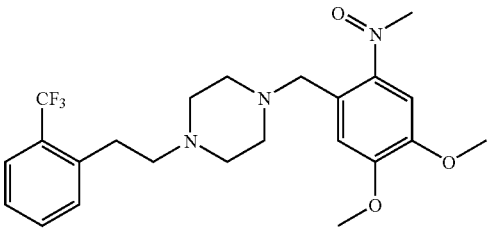 | [M + H]+: 454 |
| 100 | 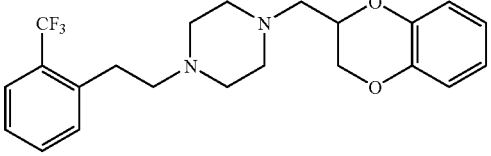 | [M + H]+: 407 |
| 101 | 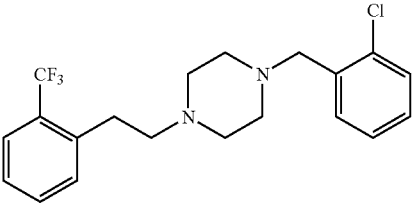 | [GC – MS]: 382 |
| 102 | 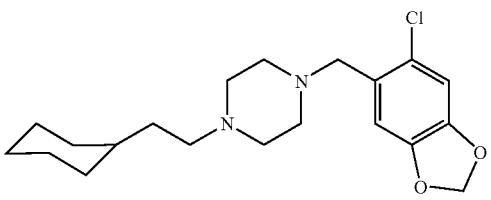 | [GC – MS]: 364 |
| 103 | 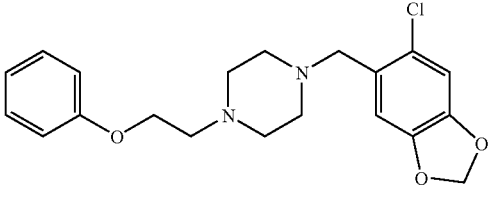 | [M + H]+: 375 |
| 104 | 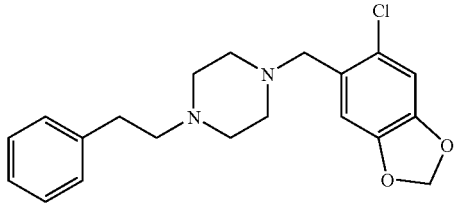 | [GC – MS]: 358 |

TABLE 1-continued
| Compound # | Structure | Characterization |
|---|---|---|
| 105 | 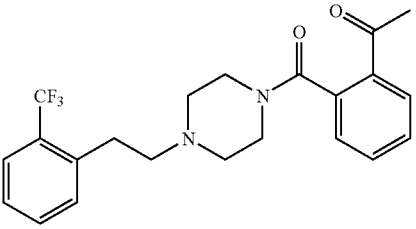 | [M + H]+: 405 |
| 106 | 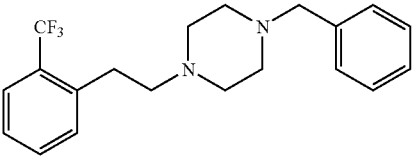 | [GC – MS]: 358 |
| 107 | 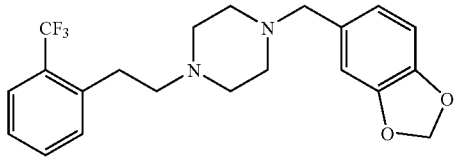 | [GC – MS]: 3927 |
| 108 | 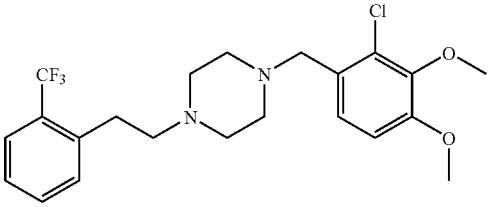 | [M + H]+: 443 |
| 109 | 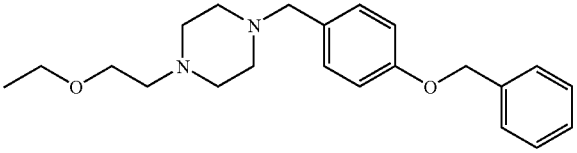 | [M + H]+: 355 |
| 110 | 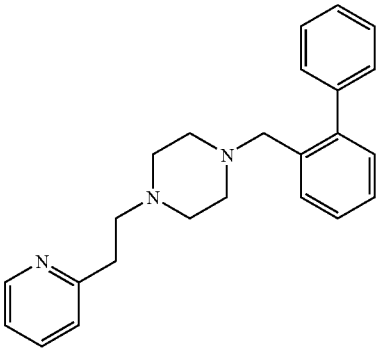 | [M + H]+: 358 |
| 111 | 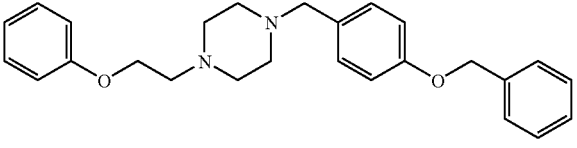 | [M + H]+: 403 |

TABLE 1-continued

| Compound # | Structure | Characterization |
|---|---|---|
| 112 | 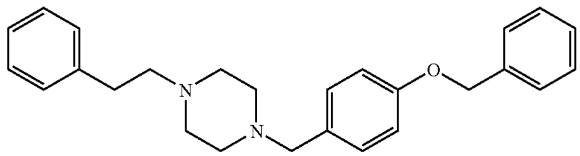 | [M + H]+: 387 |
| 113 | 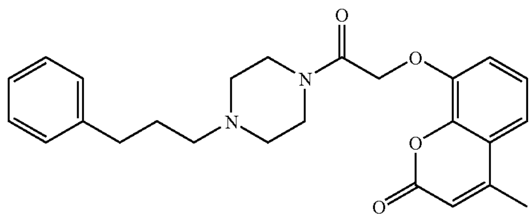 | [M + H]+: 421 |
| 114 | 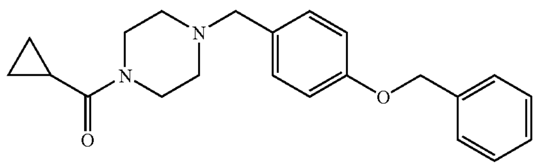 | [M + H]+: 351 |
| 115 | 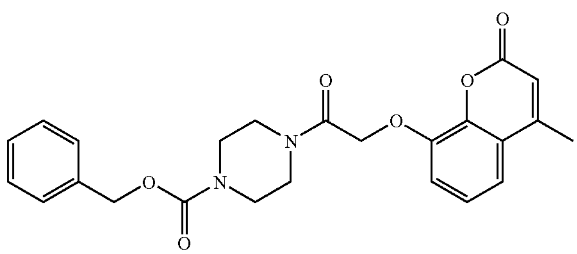 | [M + H]+: 437 |
| 116 | 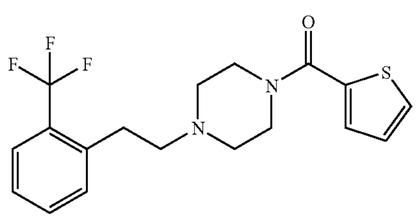 | [M + H]+: 369 |
| 117 | 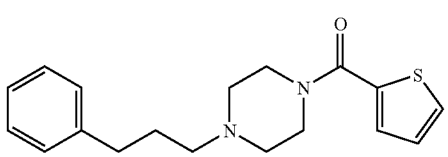 | [M + H]+: 315 |
| 118 | 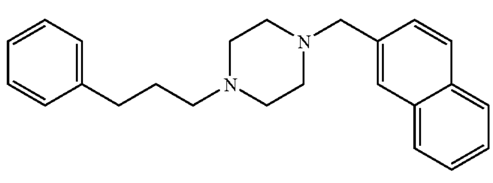 | [M + H]+: 345 |

TABLE 1-continued

| Compound # | Structure | Characterization |
|---|---|---|
| 119 | 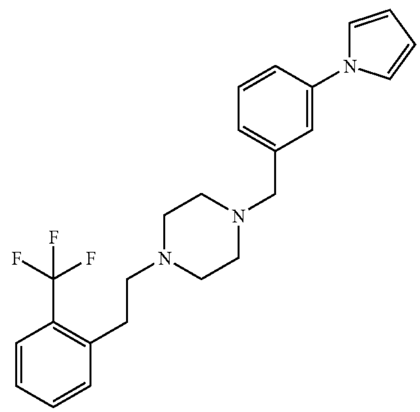 | [M + H]+: 414 |
| 120 | 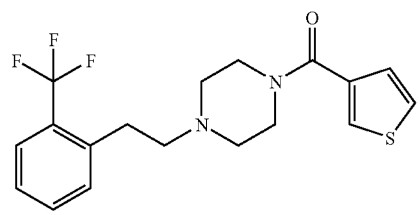 | [M + H]+: 369 |
| 121 | 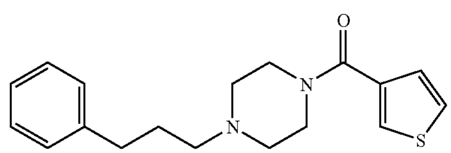 | [M + HI+: 315 |
| 122 | 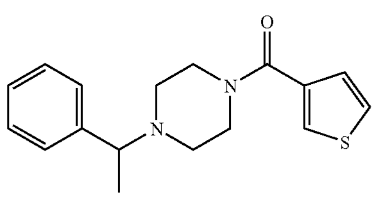 | [M + H]+: 301 |
| 123 | 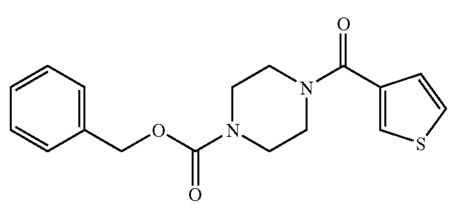 | [M + H]+: 331 |
| 124 | 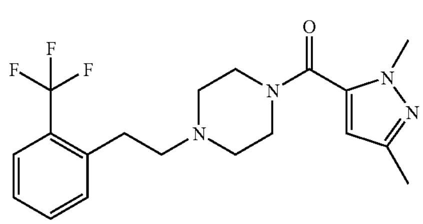 | [M + H]+: 381 |
| 125 | 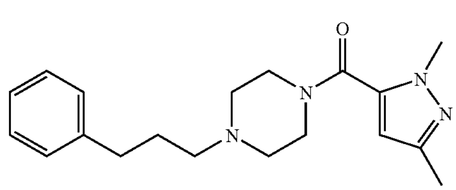 | [M + H]+: 327 |

TABLE 1-continued

| Compound # | Structure | Characterization |
|---|---|---|
| 126 | 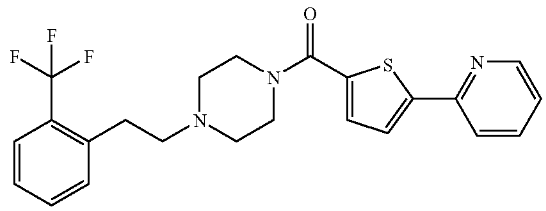 | [M + H]+: 446 |
| 127 | 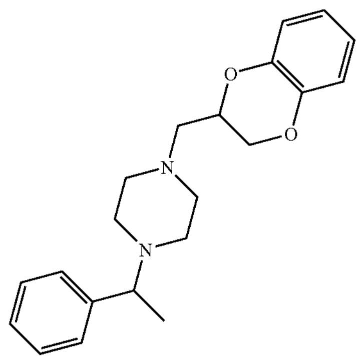 | [M + H]+: 339 |
| 128 | 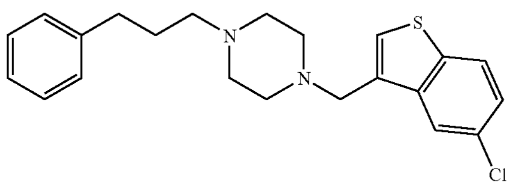 | [M + H]+: 385 |
| 129 | 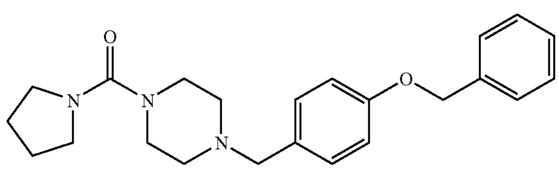 | [M + H]+: 380 |
| 130 | 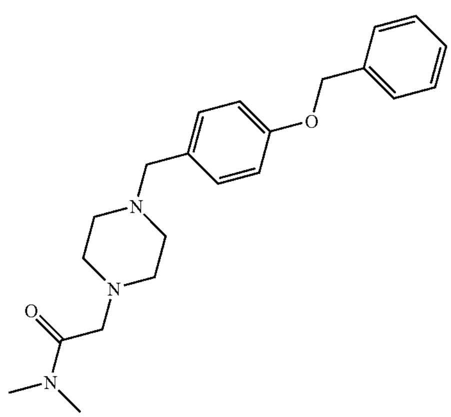 | [M + H]+: 368 |
| 131 | 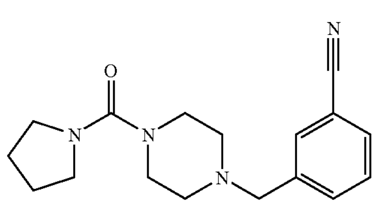 | [M + H]+: 299 |

TABLE 1-continued
| Compound # | Structure | Characterization |
|---|---|---|
| 132 | 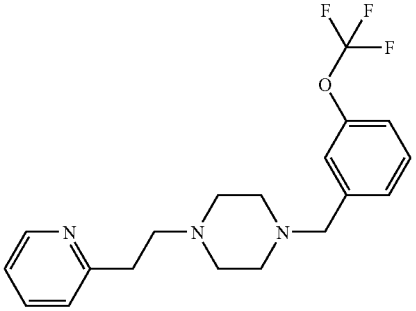 | [M + H]+: 366 |
| 133 | 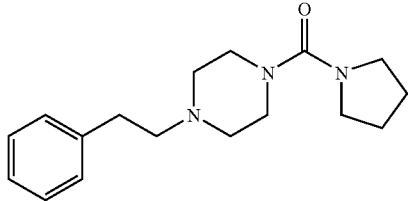 | [M + H]+: 288 |
| 134 | 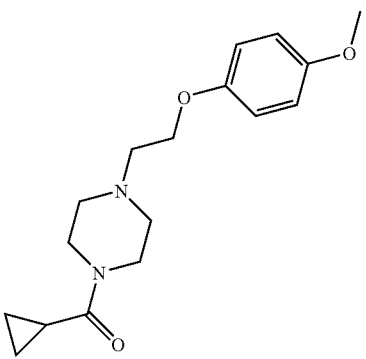 | [M + H]+: 305 |
| 135 | 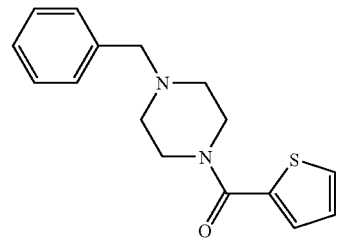 | [M + H]+: 287 |
| 136 | 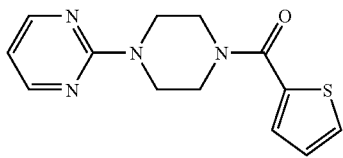 | [M + H]+: 275 |
| 137 | 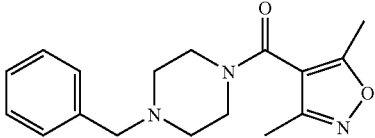 | [M + H]+: 300 |

TABLE 1-continued
| Compound # | Structure | Characterization |
|---|---|---|
| 138 | 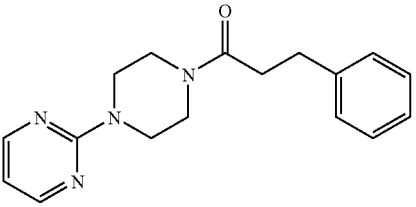 | [M + H]+: 297 |
| 139 | 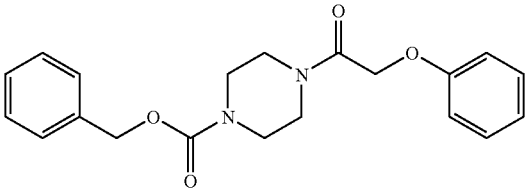 | [M + H]+: 355 |
| 140 | 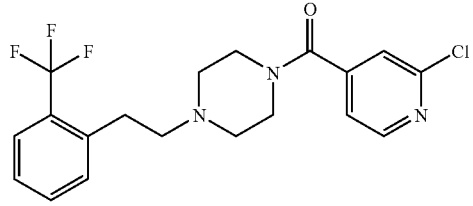 | [M + H]+: 398 |
| 141 | 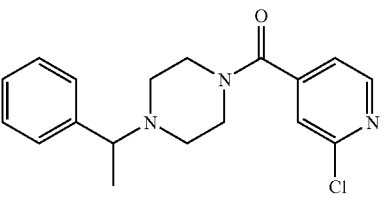 | [M + H]+: 330 |
| 142 | 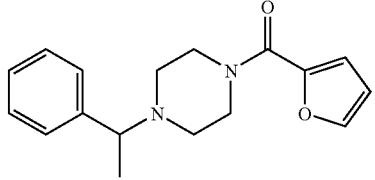 | [M + H]+: 285 |
| 143 | 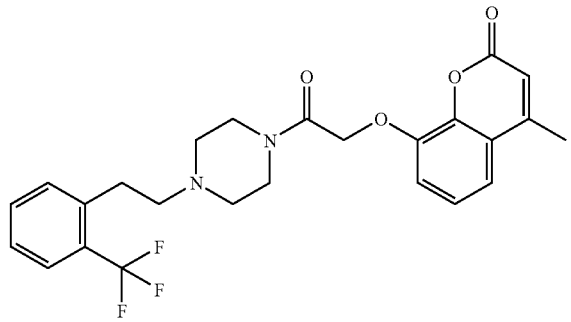 | [M + H]+: 475 |

TABLE 1-continued

| Compound # | Structure | Characterization |
|---|---|---|
| 144 | 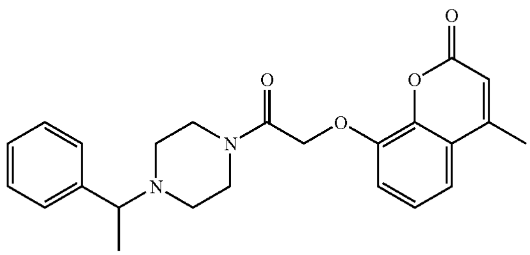 | [M + H]+: 407 |
| 145 | 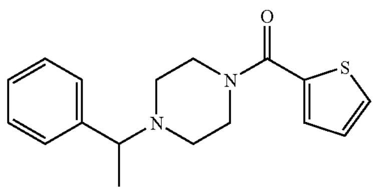 | [M + H]+: 301 |
| 146 | 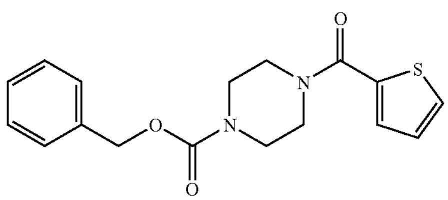 | [M + H]+: 331 |
| 147 | 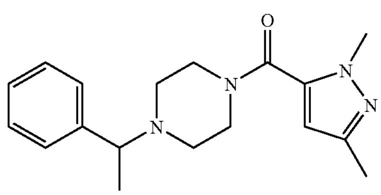 | [M + H]+: 313 |
| 148 | 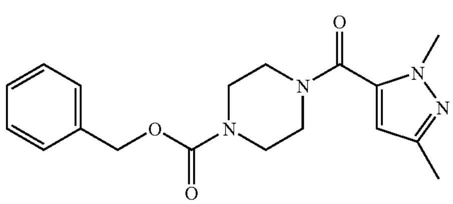 | [M + H]+: 343 |
| 149 | 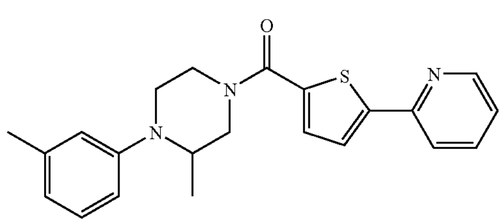 | [M + H]+: 378 |
| 150 | 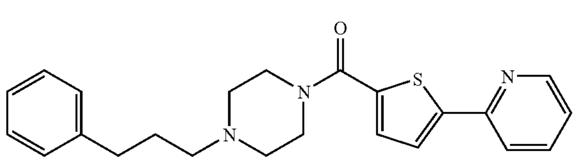 | [M + H]+: 392 |

TABLE 1-continued

| Compound # | Structure | Characterization |
| --- | --- | --- |
| 151 | 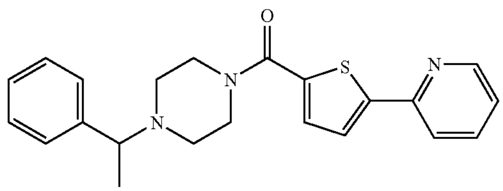 | [M + H]+: 378 |
| 152 | 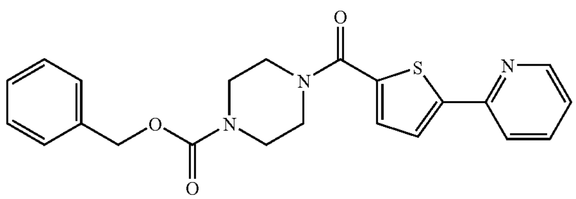 | [M + H]+: 408 |
| 153 | 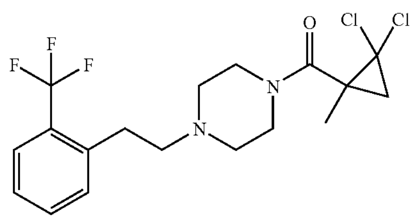 | [M + H]+: 410 |
| 154 | 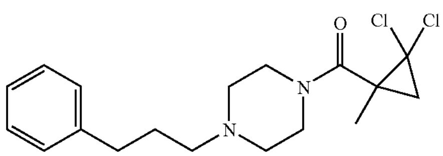 | [M + H]+: 356 |
| 155 | 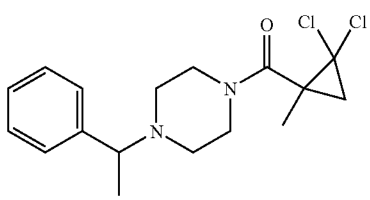 | [M + H]+: 342 |
| 156 | 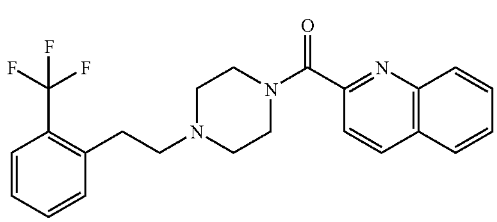 | [M + H]+: 414 |
| 157 | 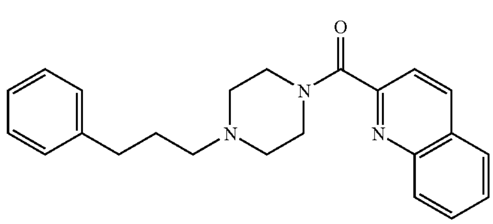 | [M + H]+: 360 |

TABLE 1-continued

| Compound # | Structure | Characterization |
|---|---|---|
| 158 | 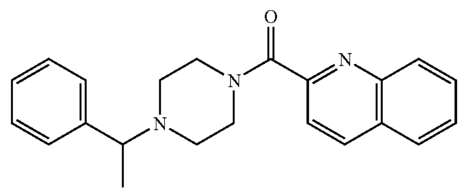 | [M + H]+: 346 |
| 159 | 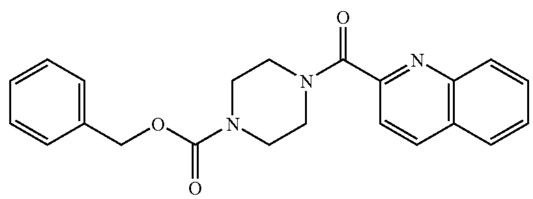 | [M + H]+: 376 |
| 160 | 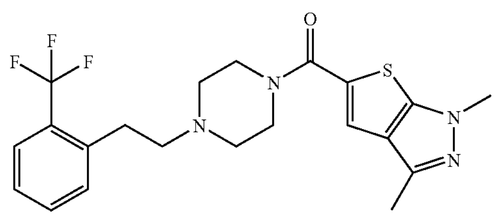 | [M + H]+: 437 |
| 161 | 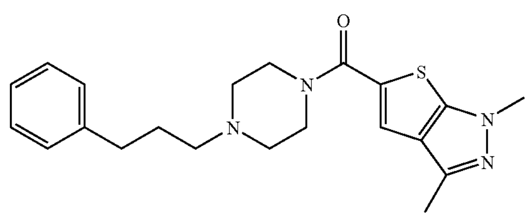 | [M + H]+: 382 |
| 162 | 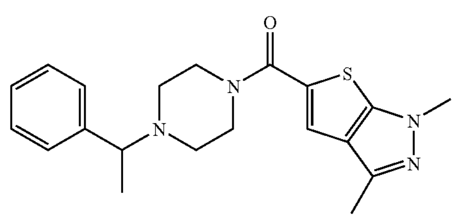 | [M + H]+: 369 |
| 163 | 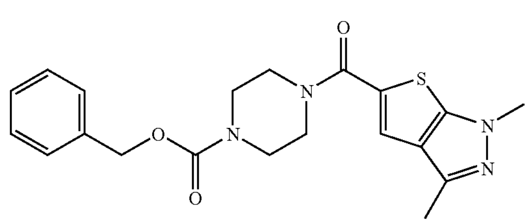 | [M + H]+: 399 |
| 164 | 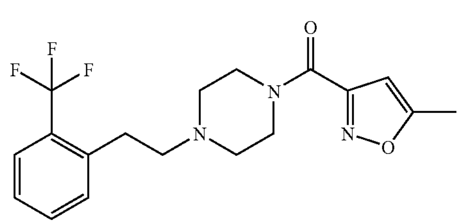 | [M + H]+: 368 |

TABLE 1-continued

| Compound # | Structure | Characterization |
|---|---|---|
| 165 | 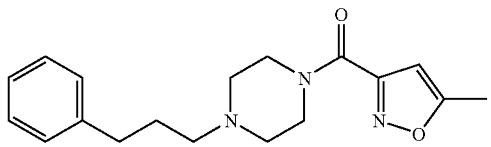 | [M + H]+: 314 |
| 166 | 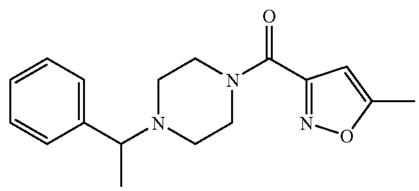 | [M + H]+: 300 |
| 167 | 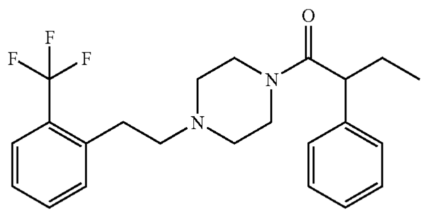 | [M + H]+: 405 |
| 168 | 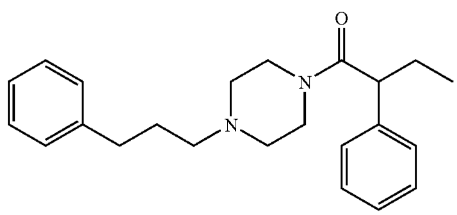 | [M + H]+: 351 |
| 169 | 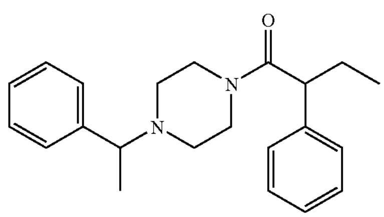 | [M + H]+: 337 |
| 170 | 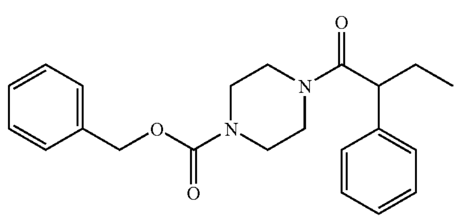 | [M + H]+: 367 |
| 171 | 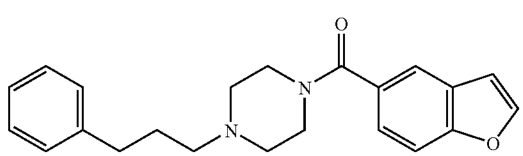 | [M + H]+: 349 |
| 172 | 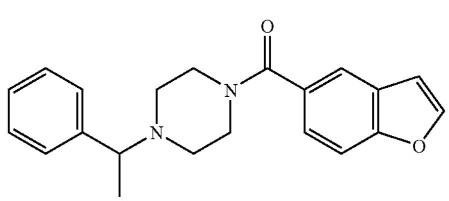 | [M + H]+: 335 |

TABLE 1-continued

| Compound # | Structure | Characterization |
|---|---|---|
| 173 | 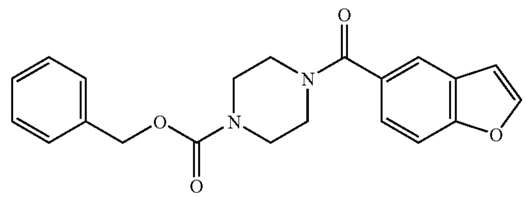 | [M + H]+: 365 |
| 174 | 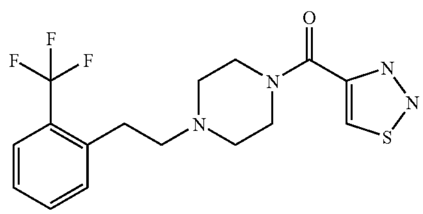 | [M + H]+: 371 |
| 175 | 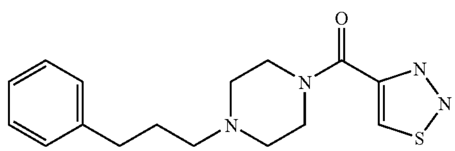 | [M + H]+: 317 |
| 176 | 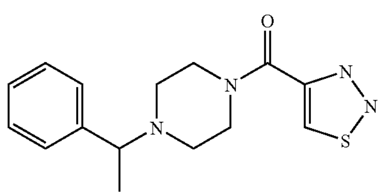 | [M + H]+: 303 |
| 177 | 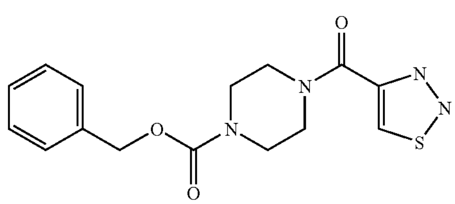 | [M + H]+: 333 |
| 178 | 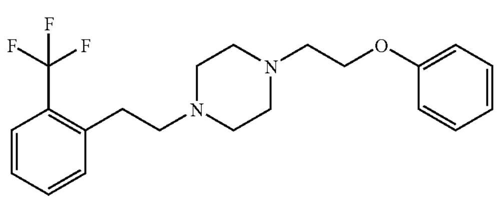 | [M + H]+: 379 |
| 179 | 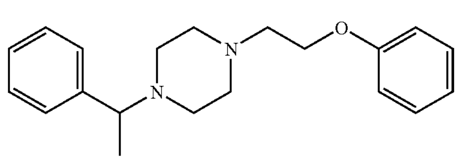 | [M + H]+: 311 |
| 180 | 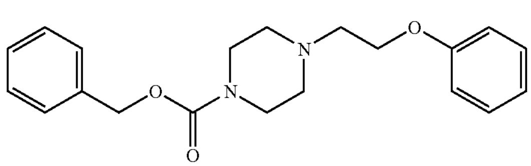 | [M + H]+: 341 |

TABLE 1-continued

| Compound # | Structure | Characterization |
|---|---|---|
| 181 | 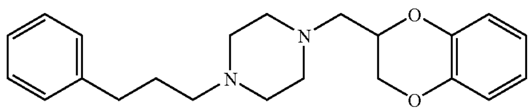 | [M + H]+: 353 |
| 182 | 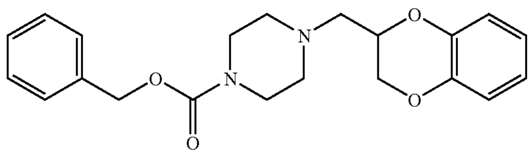 | [M + H]+: 369 |
| 183 | 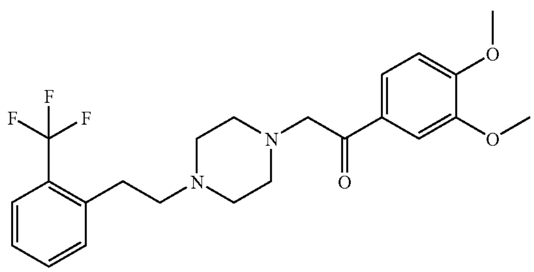 | [M + H]+: 437 |
| 184 | 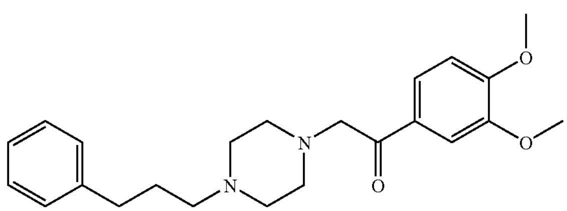 | [M + H]+: 383 |
| 185 | 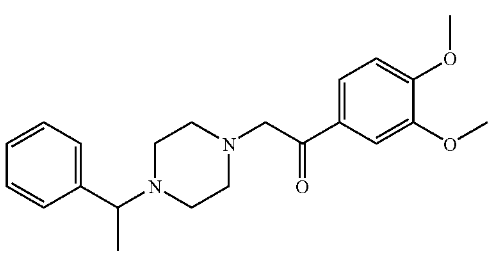 | [M + H]+: 369 |
| 186 | 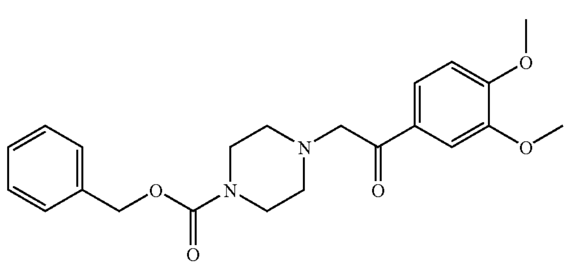 | [M + H]+: 399 |
| 187 | 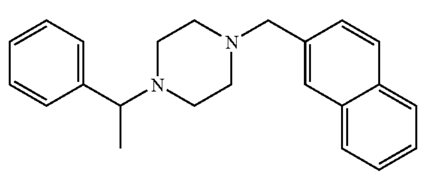 | [M + H]+: 331 |

TABLE 1-continued

| Compound # | Structure | Characterization |
|---|---|---|
| 188 | 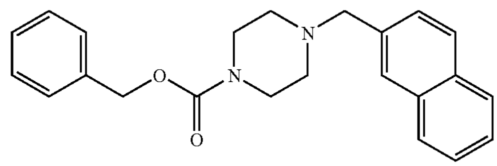 | [M + H]+: 361 |
| 189 | 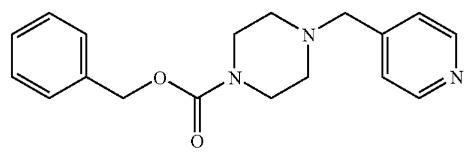 | [M + H]+: 312 |
| 190 | 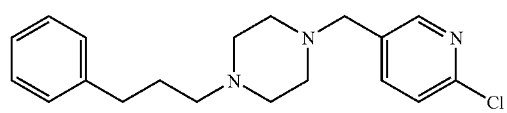 | [M + H]+: 330 |
| 191 | 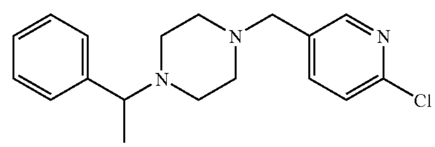 | [M + H]+: 316 |
| 192 | 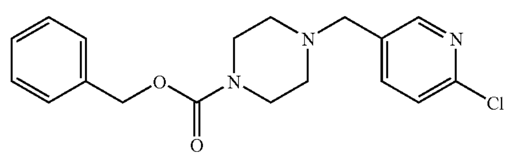 | [M + H]+: 346 |
| 193 | 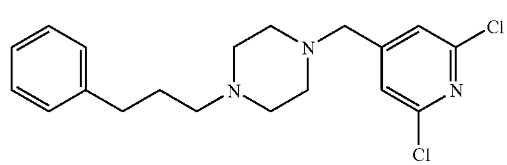 | [M + H]+: 365 |
| 194 | 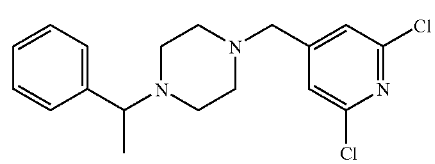 | [M + H]+: 351 |
| 195 | 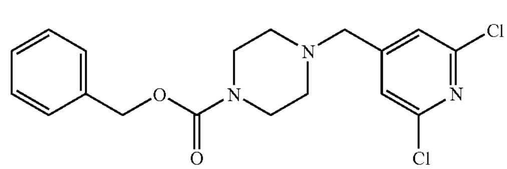 | [M + H]+: 381 |
| 196 | 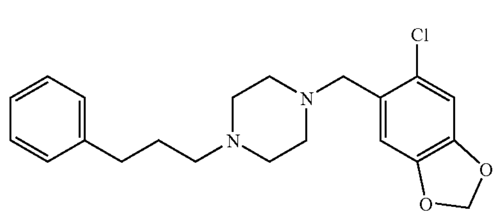 | [M + H]+: 373 |

TABLE 1-continued

| Compound # | Structure | Characterization |
|---|---|---|
| 197 | 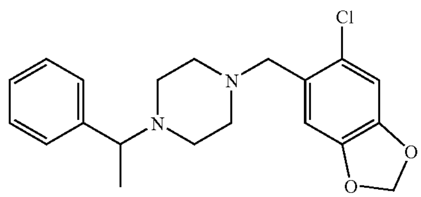 | [M + H]+: 359 |
| 198 | 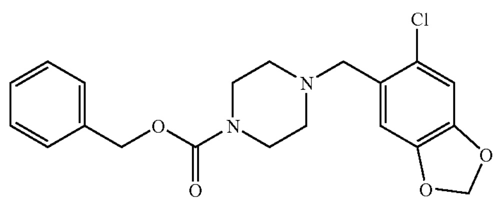 | [M + H]+: 389 |
| 199 | 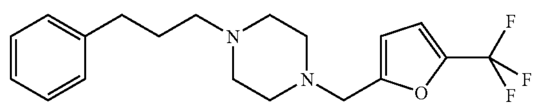 | [M + H]+: 353 |
| 200 | 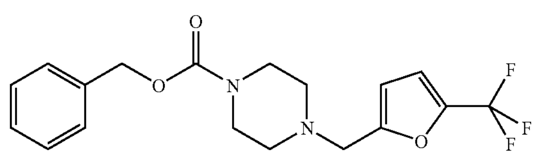 | [M + H]+: 369 |
| 201 | 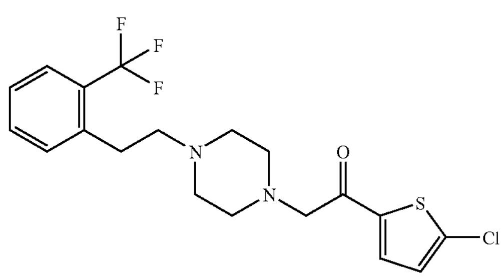 | [M + H]+: 417 |
| 202 | 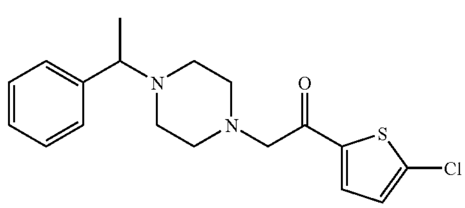 | [M + H]+: 349 |
| 203 | 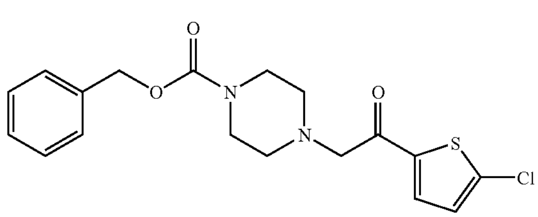 | [M + H]+: 379 |

TABLE 1-continued

| Compound # | Structure | Characterization |
|---|---|---|
| 204 | 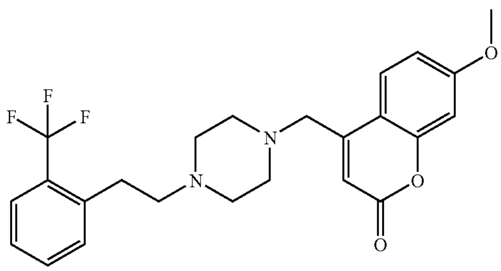 | [M + H]+: 447 |
| 205 | 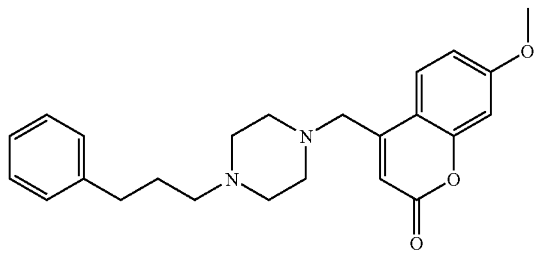 | [M + H]+: 393 |
| 206 | 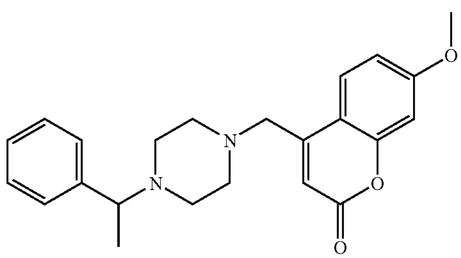 | [M + H]+: 379 |
| 207 | 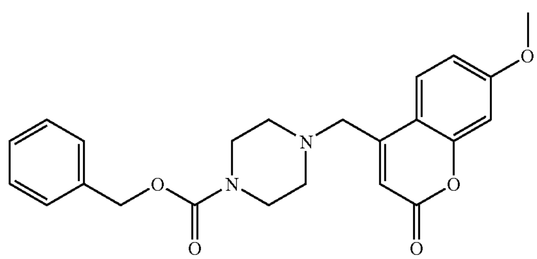 | [M + H]+: 409 |
| 208 | 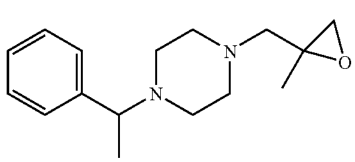 | [M + H]+: 261 |
| 209 | 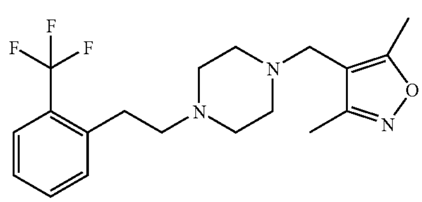 | [M + H]+: 368 |
| 210 | 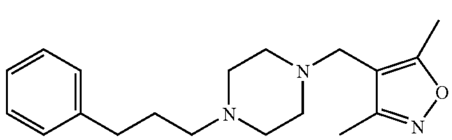 | [M + H]+: 314 |

TABLE 1-continued

| Compound # | Structure | Characterization |
|---|---|---|
| 211 | 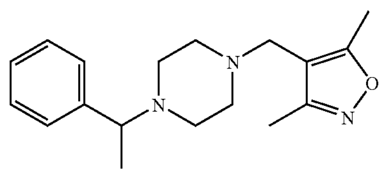 | [M + H]+: 300 |
| 212 | 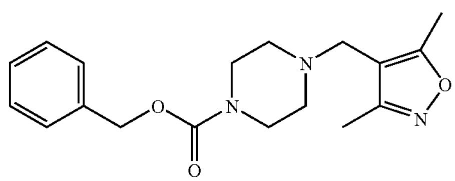 | [M + H]+: 330 |
| 213 | 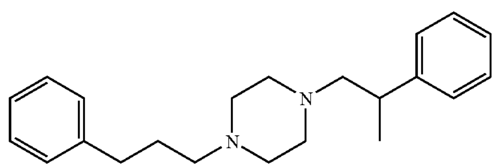 | [M + H]+: 323 |
| 214 | 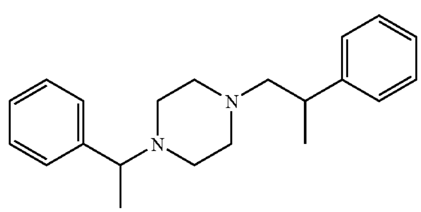 | [M + H]+: 309 |
| 215 | 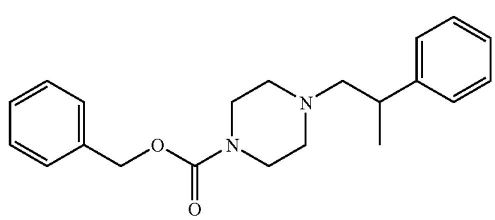 | [M + H]+: 339 |
| 216 | 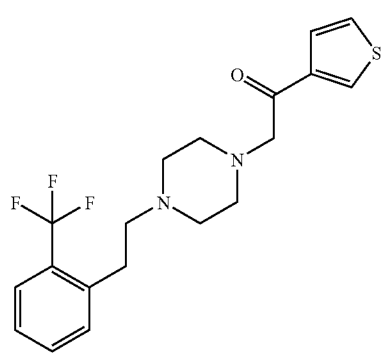 | [M + H]+: 383 |

TABLE 1-continued

| Compound # | Structure | Characterization |
|---|---|---|
| 217 | 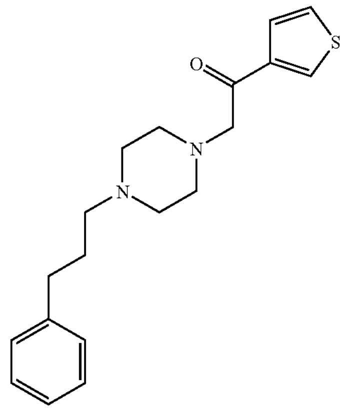 | [M + H]+: 329 |
| 218 | 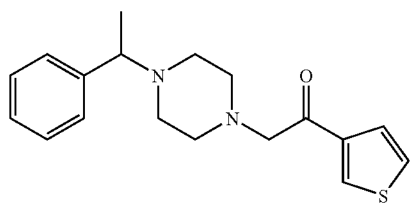 | [M + H]+: 315 |
| 219 | 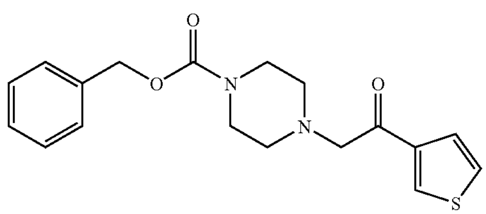 | [M + H]+: 345 |
| 220 | 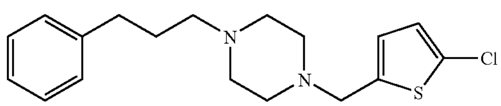 | [M + H]+: 335 |
| 221 | 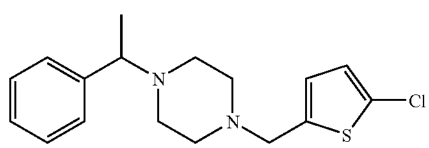 | [M + H]+: 321 |
| 222 | 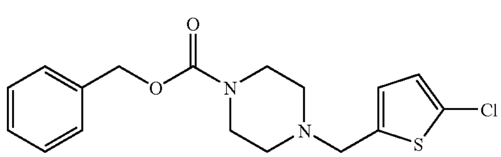 | [M + H]+: 351 |
| 223 | 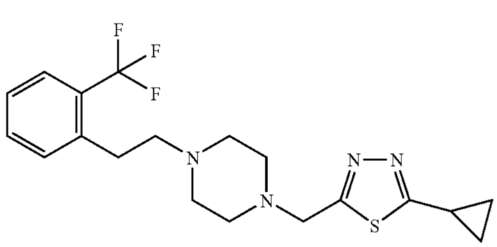 | [M + H]+: 397 |

TABLE 1-continued

| Compound # | Structure | Characterization |
|---|---|---|
| 224 | 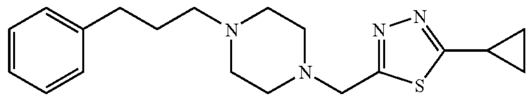 | [M + H]+: 343 |
| 225 | 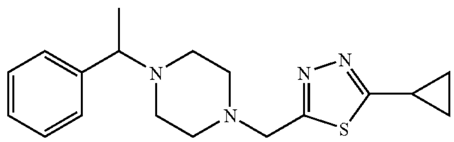 | [M + H]+: 329 |
| 226 | 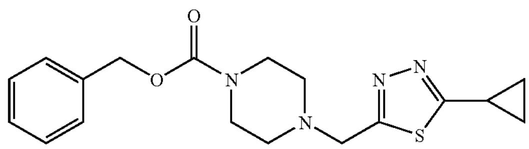 | [M + H]+: 359 |
| 227 | 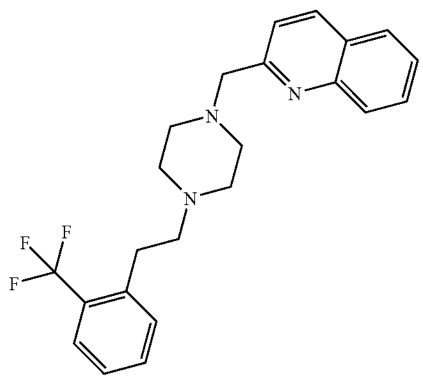 | [M + H]+: 400 |
| 228 | 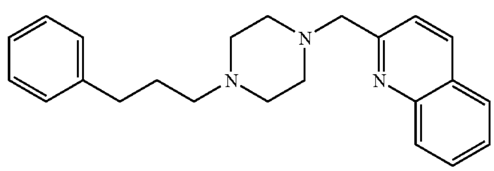 | [M + H]+: 346 |
| 229 | 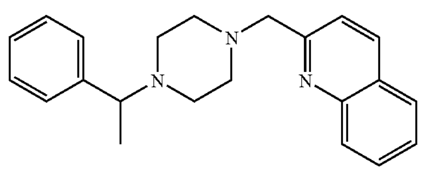 | [M + H]+: 332 |
| 230 | 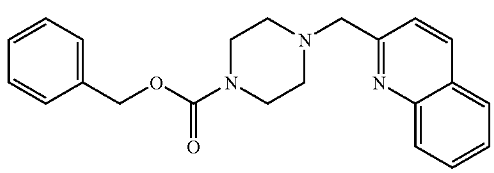 | [M + H]+: 362 |
| 231 | 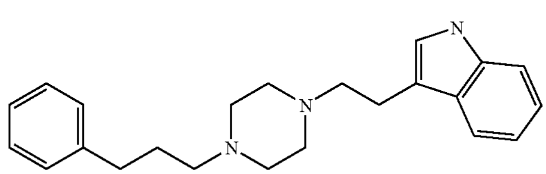 | [M + H]+: 348 |

TABLE 1-continued

| Compound # | Structure | Characterization |
|---|---|---|
| 232 | 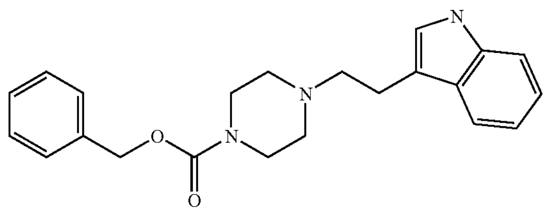 | [M + H]+: 364 |
| 233 | 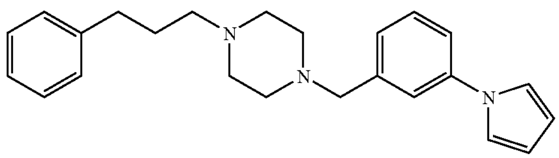 | [M + H]+: 360 |
| 234 | 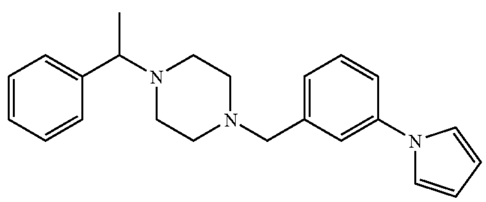 | [M + H]+: 346 |
| 235 | 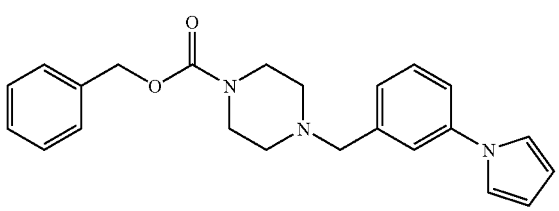 | [M + H]+: 376 |
| 236 | 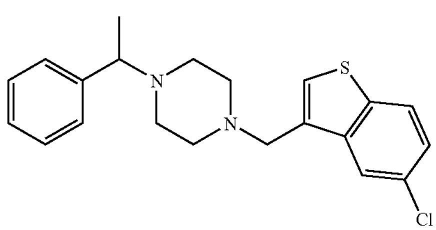 | [M + H]+: 371 |
| 237 | 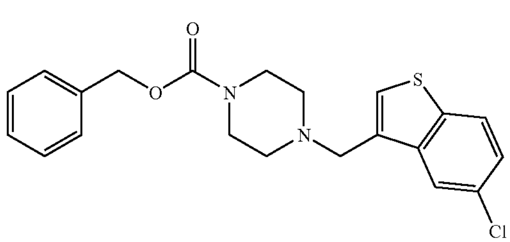 | [M + H]+: 401 |
| 238 | 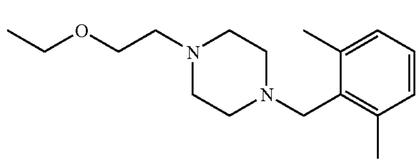 | [M + H]+: 277 |

TABLE 1-continued

| Compound # | Structure | Characterization |
|---|---|---|
| 239 | 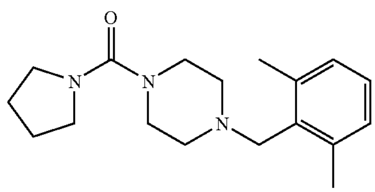 | [M + H]+: 302 |
| 240 | 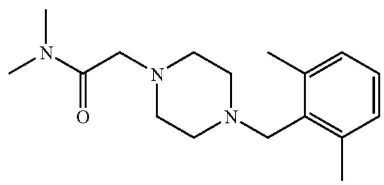 | [M + H]+: 290 |
| 241 | 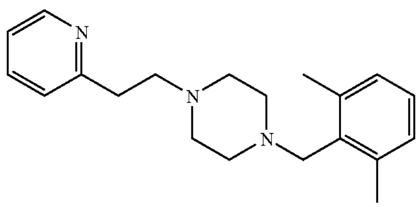 | [M + H]+: 310 |
| 242 | 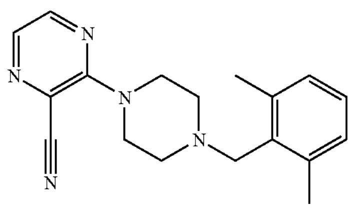 | [M + H]+: 308 |
| 243 | 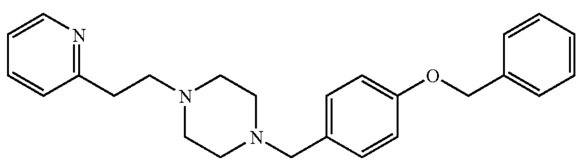 | [M + H]+: 388 |
| 244 | 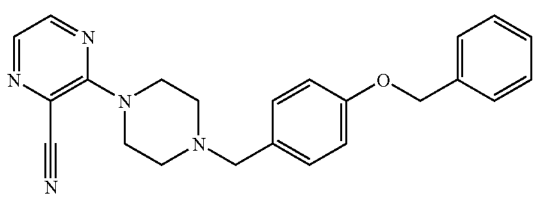 | [M + H]+: 386 |
| 245 | 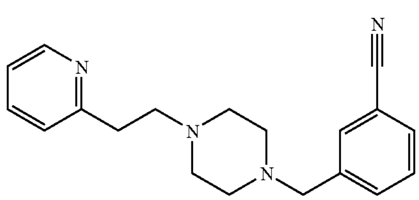 | [M + H]+: 307 |
| 246 | 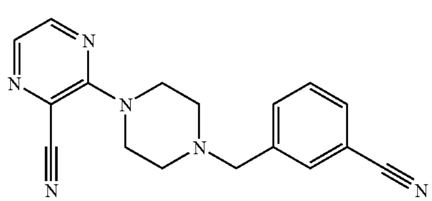 | [M + H]+: 305 |

TABLE 1-continued

| Compound # | Structure | Characterization |
|---|---|---|
| 247 | 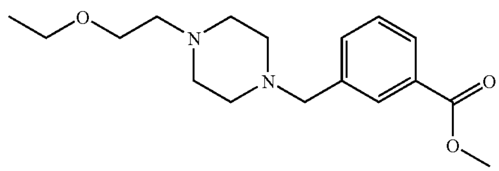 | [M+ H]+: 307 |
| 248 | 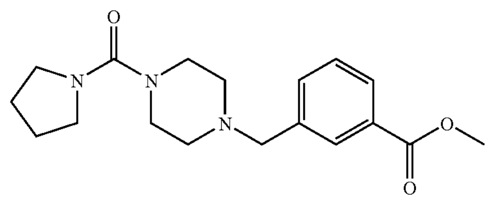 | [M + H]+: 332 |
| 249 | 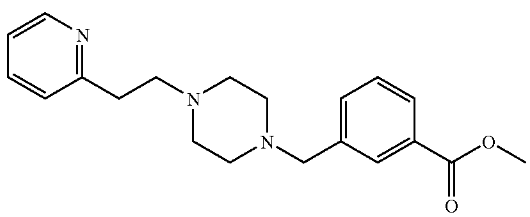 | [M + H]+: 340 |
| 250 | 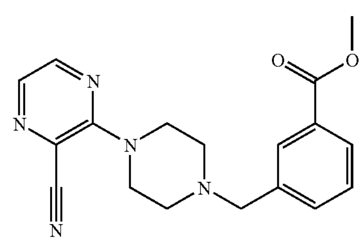 | [M + H]+: 338 |
| 251 | 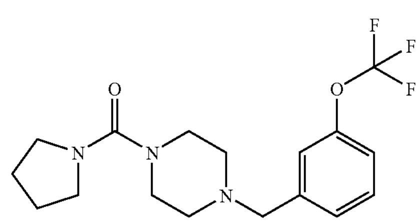 | [M + H]+: 358 |
| 252 | 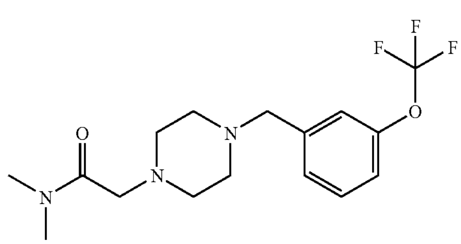 | [M + H]+: 346 |
| 253 | 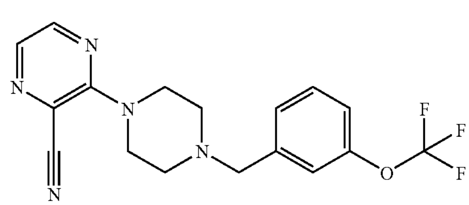 | [M + H]+: 364 |

TABLE 1-continued

| Compound # | Structure | Characterization |
|---|---|---|
| 254 | 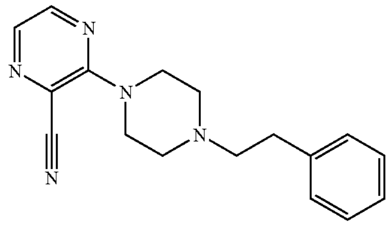 | [M + H]+: 294 |
| 255 | 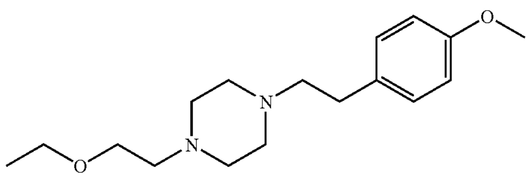 | [M + H]+: 293 |
| 256 | 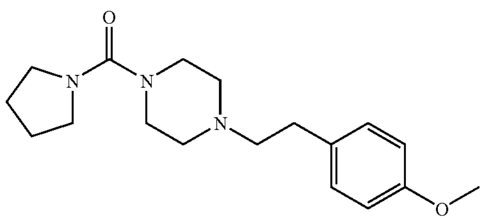 | [M + HI]+: 318 |
| 257 | 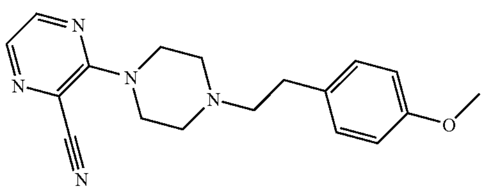 | [M + H]+: 324 |
| 258 | 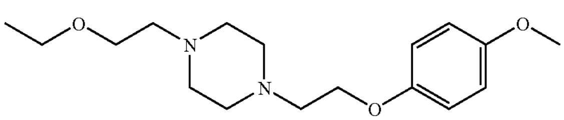 | [M + H]+: 309 |
| 259 | 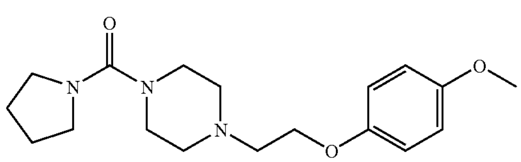 | [M + H]+: 334 |
| 260 | 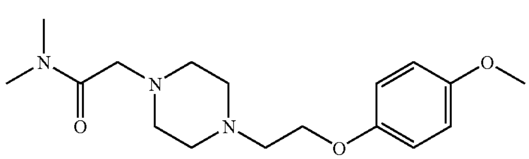 | [M + H]+: 322 |
| 261 | 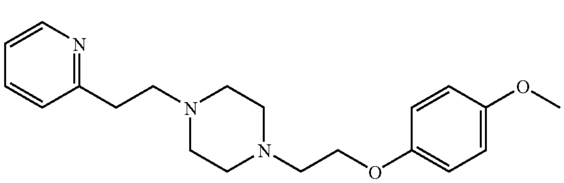 | [M + H]+: 342 |

TABLE 1-continued

| Compound # | Structure | Characterization |
|---|---|---|
| 262 | 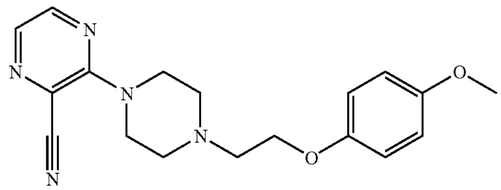 | [M + H]+: 340 |
| 263 | 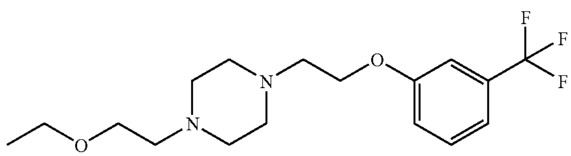 | [M + H]+: 347 |
| 264 | 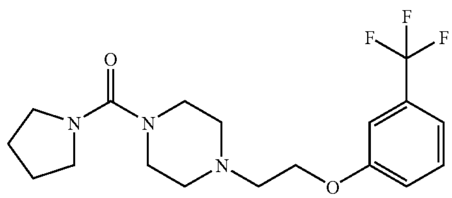 | [M + H]+: 372 |
| 265 | 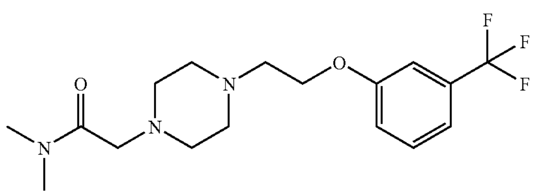 | [M + H]+: 360 |
| 266 | 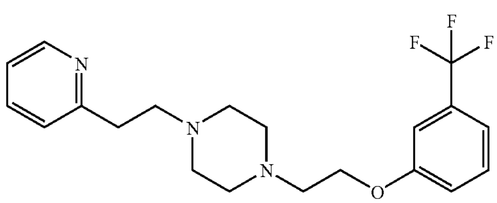 | [M + H]+: 380 |
| 267 | 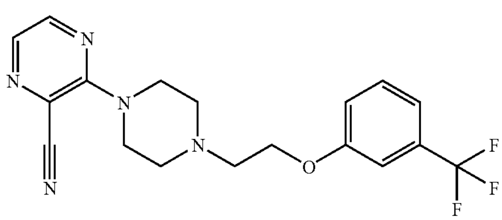 | [M + H]+: 378 |
| 268 | 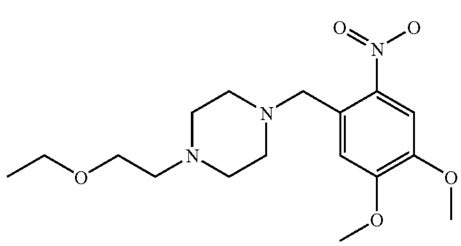 | [M + H]+: 354 |

TABLE 1-continued

| Compound # | Structure | Characterization |
|---|---|---|
| 269 | 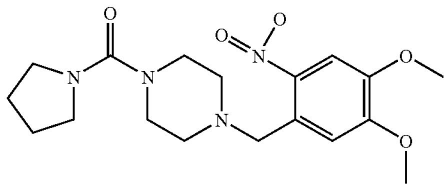 | [M + H]+: 379 |
| 270 | 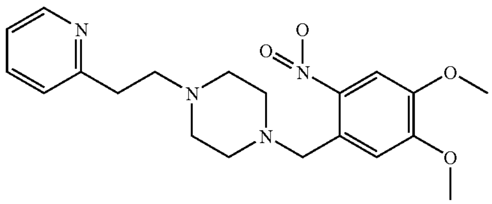 | [M + H]+: 387 |
| 271 | 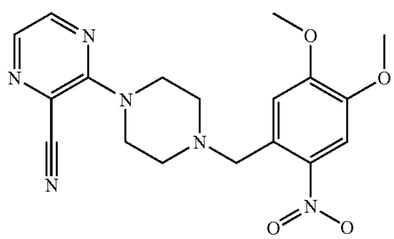 | [M + H]+: 387 |
| 272 | 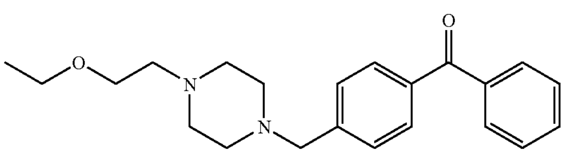 | [M + H]+: 353 |
| 273 | 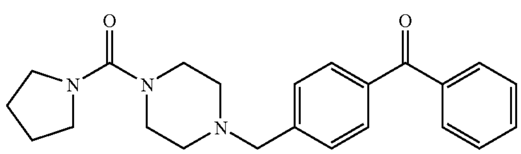 | [M + H]+: 378 |
| 274 | 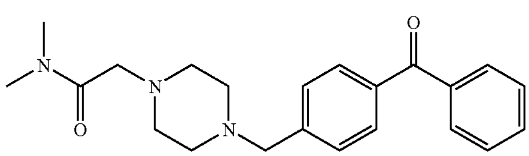 | [M + H]+: 366 |
| 275 | 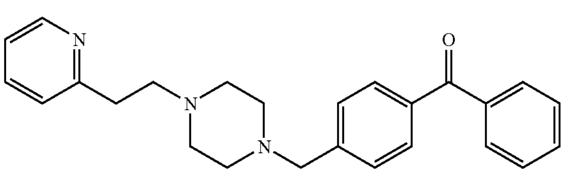 | [M + H]+: 386 |
| 276 | 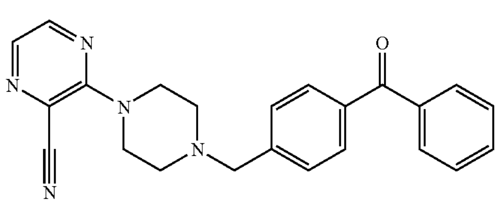 | [M + H]+: 384 |

TABLE 1-continued

| Compound # | Structure | Characterization |
|---|---|---|
| 277 | 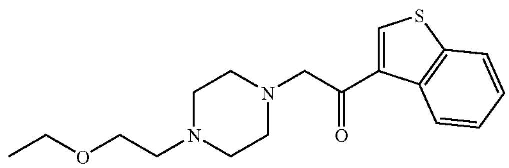 | [M + H]+: 333 |
| 278 | 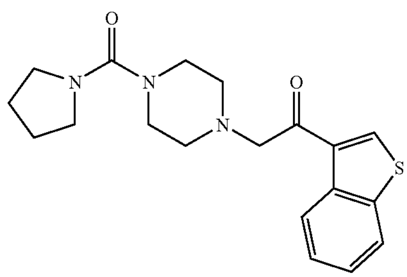 | [M + H]+: 358 |
| 279 | 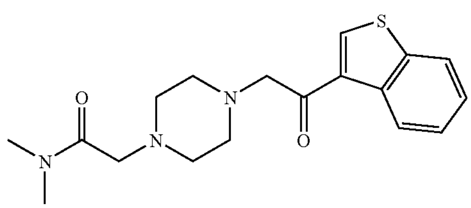 | [M + H]+: 346 |
| 280 | 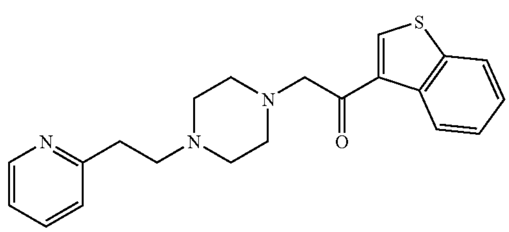 | [M + H]+: 366 |
| 281 | 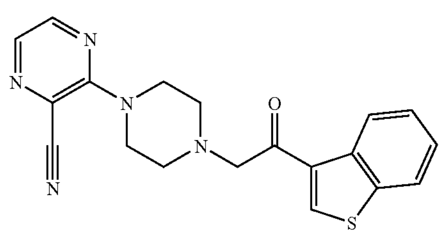 | [M + H]+: 364 |
| 282 | 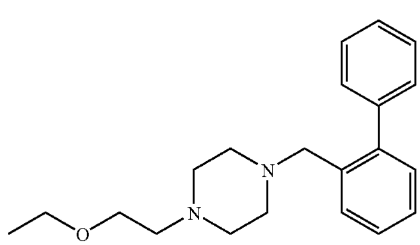 | [M + H]+: 325 |

TABLE 1-continued

| Compound # | Structure | Characterization |
|---|---|---|
| 283 | 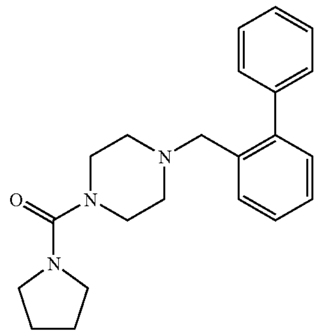 | [M + H]+: 350 |
| 284 | 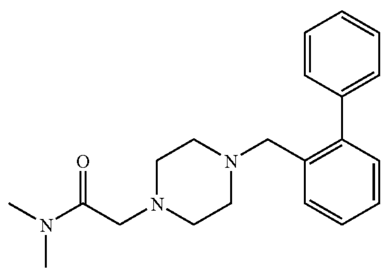 | [M + H]+: 338 |
| 285 | 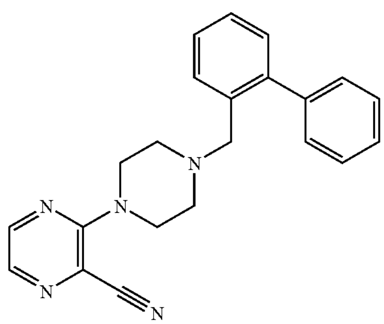 | [M + H]+: 356 |
| 286 | 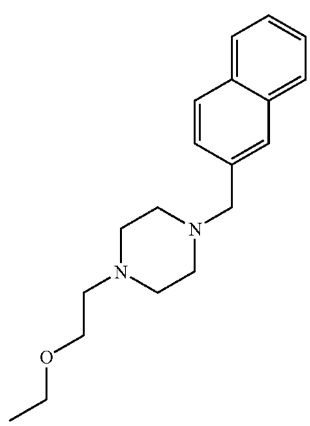 | [M + H]+: 299 |
| 287 | 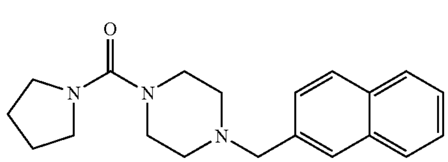 | [M + H]+: 324 |

TABLE 1-continued
| Compound # | Structure | Characterization |
|---|---|---|
| 288 | 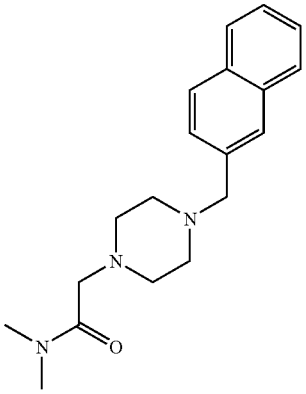 | [M + H]+: 312 |
| 289 | 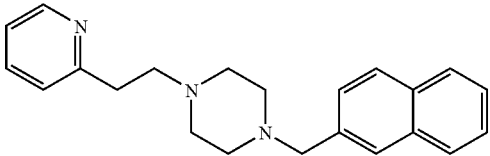 | [M + H]+: 332 |
| 290 | 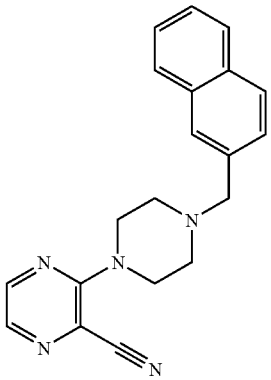 | [M + H]+: 330 |
| 291 | 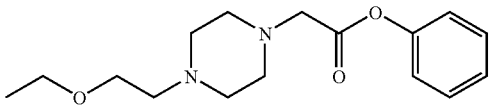 | [M + H]+: 293 |
| 292 | 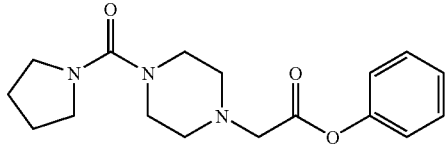 | [M + H]+: 318 |
| 293 | 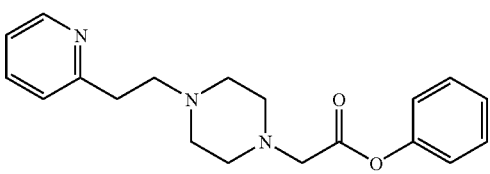 | [M + H]+: 326 |

TABLE 1-continued

| Compound # | Structure | Characterization |
|---|---|---|
| 294 | 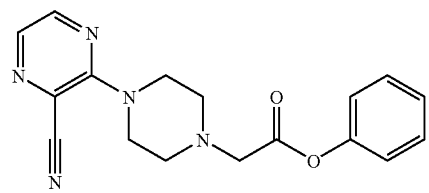 | [M + H]+: 324 |
| 295 | 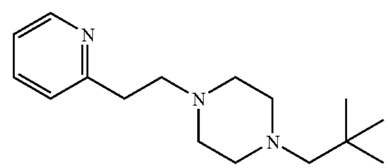 | [M + H]+: 262 |
| 296 | 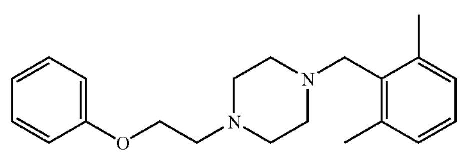 | [M + H]+: 325 |
| 297 | 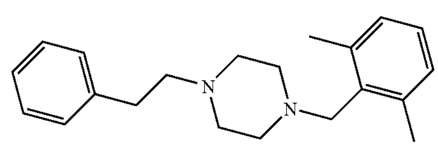 | [M + H]+: 309 |
| 298 | 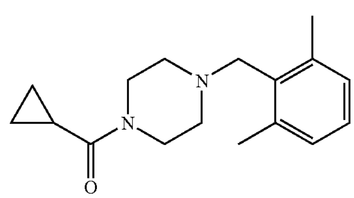 | [M + H]+: 273 |
| 299 | 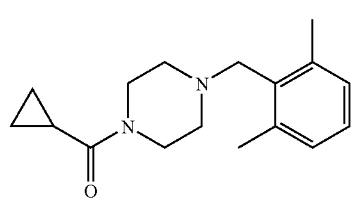 | [M + H]+: 340 |
| 300 | 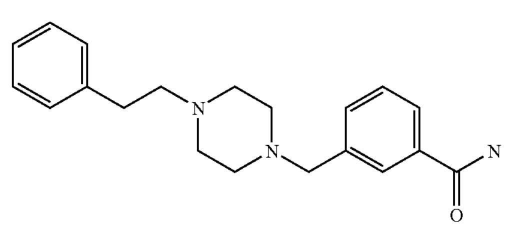 | [M + H]+: 324 |
| 301 | 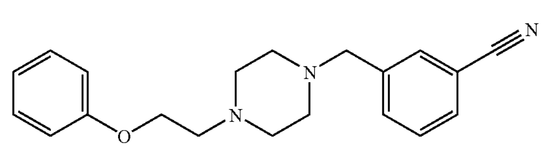 | [M + H]+: 322 |

TABLE 1-continued

| Compound # | Structure | Characterization |
|---|---|---|
| 302 | 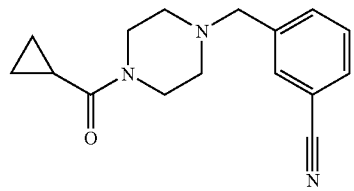 | [M + H]+: 270 |
| 303 | 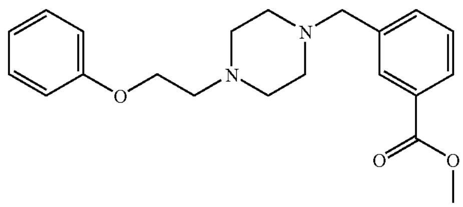 | [M + H]+: 355 |
| 304 | 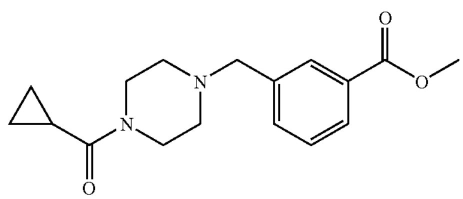 | [M + H]+: 303 |
| 305 | 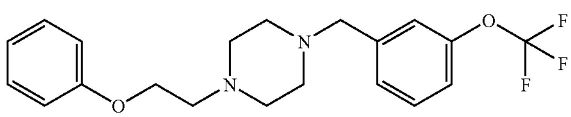 | [M + H]+: 381 |
| 306 | 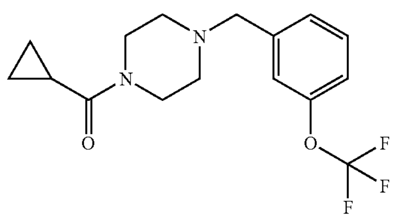 | [M + H]+: 329 |
| 307 | 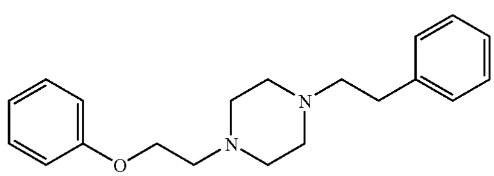 | [M + H]+: 311 |
| 308 | 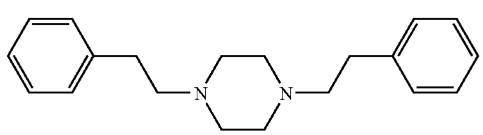 | [M + H]+: 295 |
| 309 | 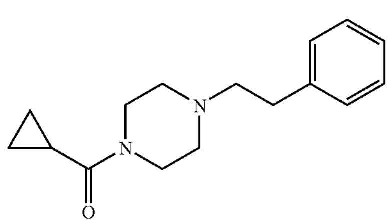 | [M + H]+: 259 |

TABLE 1-continued

| Compound # | Structure | Characterization |
|---|---|---|
| 310 | 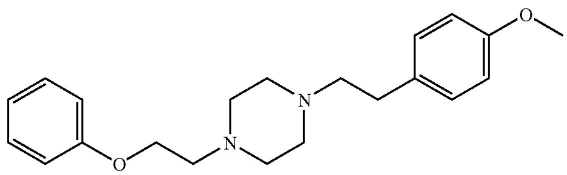 | [M + H]+: 341 |
| 311 | 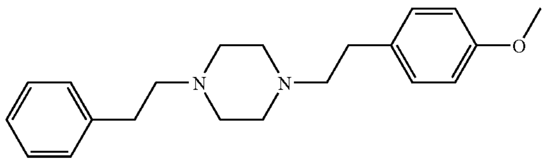 | [M + H]+: 325 |
| 312 | 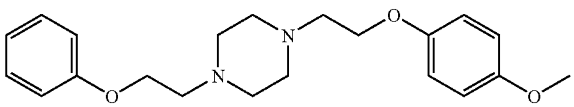 | [M + H]+: 357 |
| 313 | 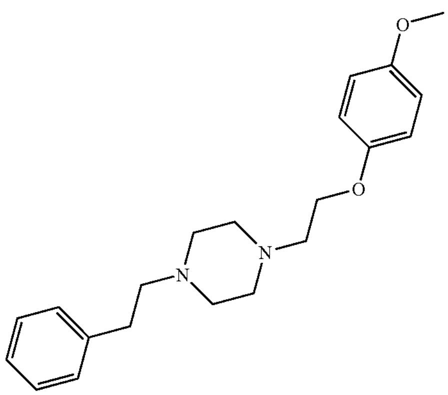 | [M + H]+: 341 |
| 314 | 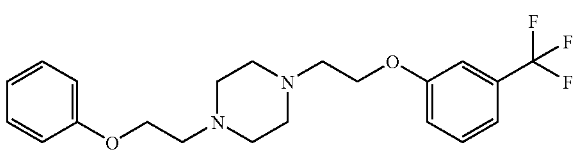 | [M + H]+: 395 |
| 315 | 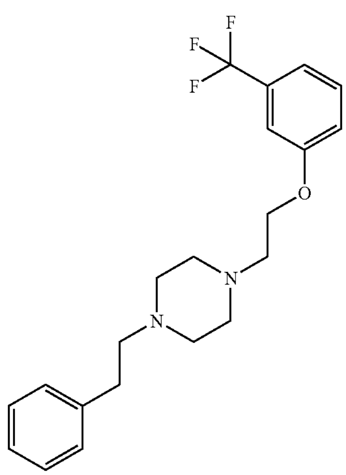 | [M + H]+: 379 |

TABLE 1-continued

| Compound # | Structure | Characterization |
|---|---|---|
| 316 | 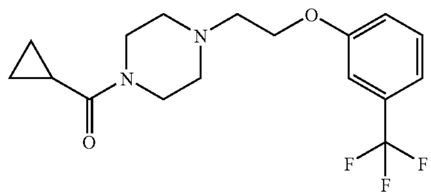 | [M + H]+: 343 |
| 317 | 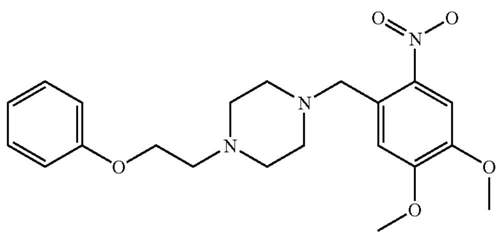 | [M + H]+: 402 |
| 318 | 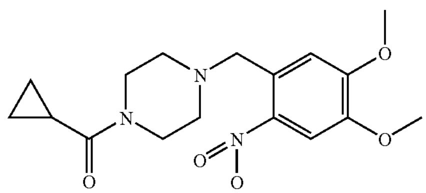 | [M + H]+: 350 |
| 319 | 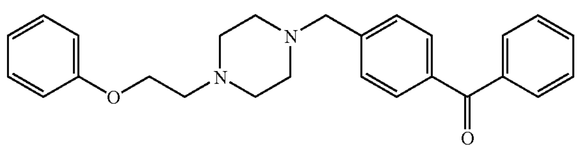 | [M + H]+: 401 |
| 320 | 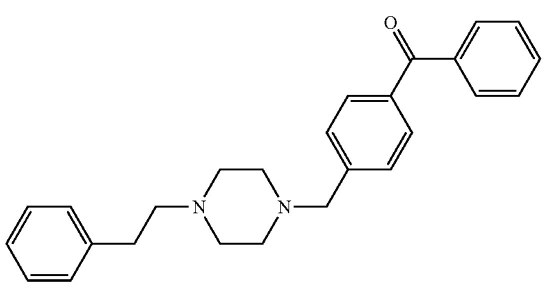 | [M + H]+: 385 |
| 321 | 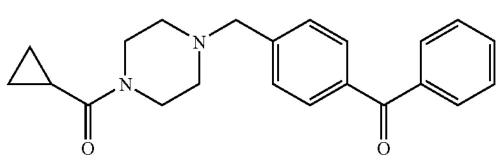 | [M + H]+: 349 |
| 322 | 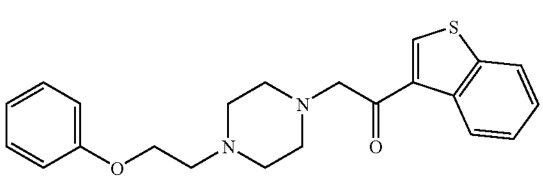 | [M + H]+: 381 |

TABLE 1-continued

| Compound # | Structure | Characterization |
|---|---|---|
| 323 | 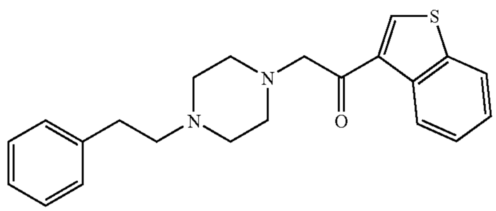 | [M + H]+: 365 |
| 324 | 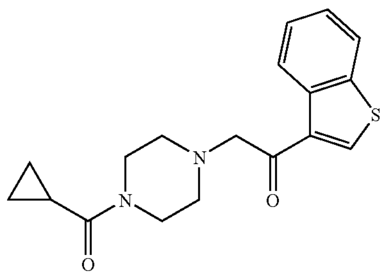 | [M + H]+: 329 |
| 325 | 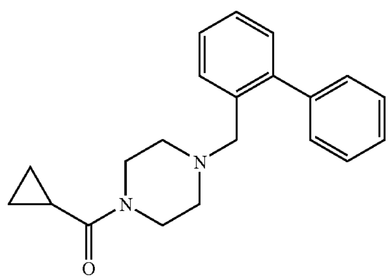 | [M + H]+: 321 |
| 326 | 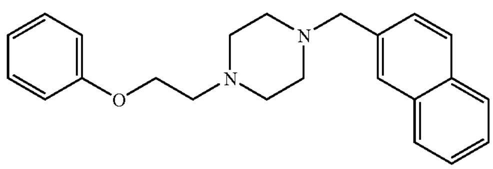 | [M + H]+: 347 |
| 327 | 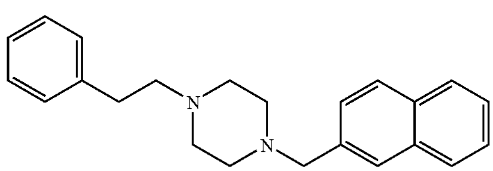 | [M + H]+: 331 |
| 328 | 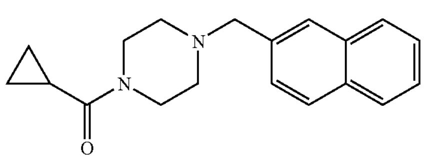 | [M + H]+: 295 |
| 329 | 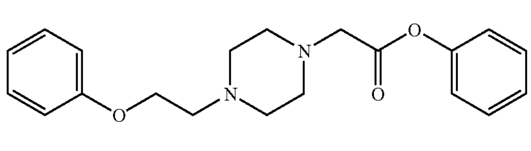 | [M + H]+: 34 |

TABLE 1-continued

| Compound # | Structure | Characterization |
|---|---|---|
| 330 | 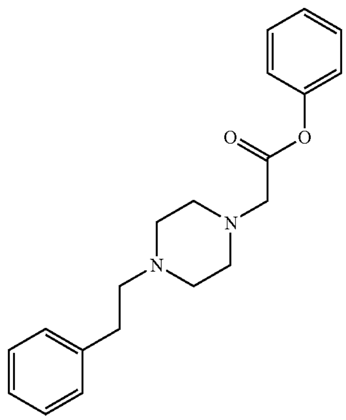 | [M + H]+: 325 |
| 331 | 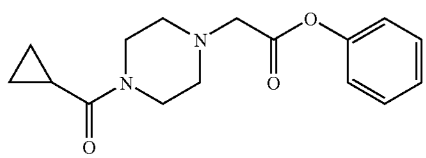 | [M + H]+: 289 |
| 332 | 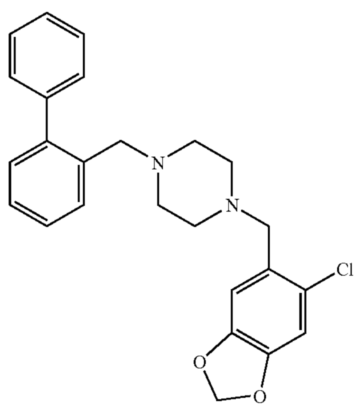 | [M + H]+: 421 |
| 333 | 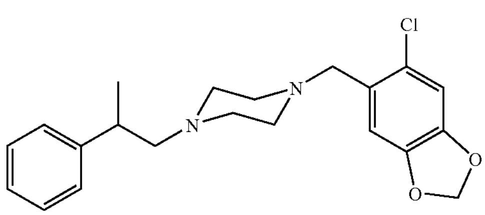 | [M + H]+: 373 |
| 334 | 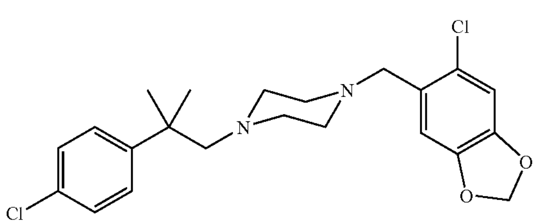 | [M + H]+: 422 |

Example VIII

Insecticidal Testing

The compounds identified in TABLE 2 were prepared using the procedures illustrated in the previous examples and these compounds were tested against beet armyworm, mosquito, fruit fly, and cotton aphid using protocols described after.

TABLE 2

| Compound # | LAPHEG | AEDSAE | DROSME | CA 200 |
|---|---|---|---|---|
| 17 | C | C | B | C |
| 34 | C | C | C | D |
| 38 | C | C | C | A |
| 44 | C | C | C | C |
| 50 | C | C | C | A |
| 80 | B | C | C | B |
| 81 | C | C | C | A |
| 86 | C | B | C | A |
| 87 | C | C | C | B |
| 88 | C | C | C | A |
| 90 | C | C | B | A |
| 91 | C | C | B | C |
| 92 | C | C | B | C |
| 93 | C | C | B | C |
| 95 | C | C | B | A |
| 96 | B | C | C | A |
| 99 | C | C | C | A |
| 100 | C | C | B | A |
| 101 | C | C | C | A |
| 102 | C | C | C | A |
| 103 | C | C | C | A |
| 104 | C | C | A | A |
| 105 | C | C | C | A |
| 106 | C | C | C | A |
| 107 | C | C | A | A |
| 108 | C | C | C | A |
| 126 | C | C | C | A |
| 139 | B | C | C | D |
| 146 | C | C | C | D |
| 156 | C | C | C | A |
| 159 | C | C | C | D |
| 160 | C | C | C | C |
| 162 | C | C | B | D |
| 192 | C | C | C | D |
| 303 | C | C | B | D |
| 321 | C | C | C | D |
| 333 | C | C | A | A |

LAPHEG refers to % mortality at 4000 µg/ml against beet armyworm on artificial diet,
AEDSAE refers to % mortality at 20 µg/ml against mosquito larvae
DROSME refers to % mortality at 4000 µg/ml against adult fruit fly on artificial diet
CA 200 refers to % control at 200 ppm against cotton aphid in foliar spray tests.
In each case of Table 2 the rating scale is as follows:

| % Mortality | Rating |
|---|---|
| 50-100 | A |
| 26-49 | B |
| 1-25 | C |
| Not tested | D |

Insecticidal Tests

Compounds were evaluated on mosquito (*Aedes aegypti*) larvae, beet armyworm (*Spodoptera exiguua*) larvae, fruit fly (*Drosophila melanogaster*) adults and cotton aphid (*Aphis gossypi*). Newly hatched mosquito larvae (about 50 larvae/well) in 96-well microtiter plates in 230 ul of water containing powdered liver/yeast extract (1 gr/100 ml) were treated with 20 ppm solution of the test compound.

Following treatment the plates were covered with a lid and mortality was determined three days after treatment. Beet armyworm eggs (about 5 per well) were placed on artificial diet (in a 96-well microtiter plate) treated with a 4000 ppm solution of a test compound in combination with piperonyl butoxide (in approximate ratio of 1:4). After infestation, the plates were covered with a lid and mortality was determined seven days following treatment. Five-day old fruit fly adults (about 5/well) were placed in deep-well microtiter plates containing 250 ul/well of a 2% agar-10% sucrose mixture that had been treated with a 4000 ppm solution of a test compound. Following infestation, the plates were covered with a lid and mortality was determined three days after treatment. Treatments for the mosquito and armyworm were replicated six times each, that of the fruit fly three times each.

Squash with fully expanded cotyledon leaves were trimmed to one cotyledon per plant and infested with cotton aphid (wingless adult and nymph) 1 day prior to chemical application. Each plant is examined before chemical application to ensure proper infestation (ca. 30-70 aphids per plant). Compounds (3 mg) were dissolved in 3 mL of acetone:methanol (50:50) solvent, forming stock solutions of 1000 ppm. The stock solutions were then diluted with 0.025% Tween 20 (in $H_2O$) to make 200 spray solutions. A hand-held Devilbiss sprayer was used to apply the spray solutions until runoff to both sides of the squash cotyledon leaves. Four plants (4 replications) were used for each concentration of each compound. Reference plants (solvent check) were sprayed with 0.025% Tween 20 only. Treated plants were held in a holding room for 3 days at approximately 23° C. and 40% RH before the number of live aphids on each plant was recorded. Insecticidal activity was measured by Corrected % Control using Abbott's correction formula and presented in TABLE 2:

Corrected % Control=$100*(X-Y)/X$ where X=No. of live aphids on solvent check plants
Y=No. of live aphids on treated plants

Example IX

Fungicidal Testing

The compounds identified in Table 4 were prepared using the procedures illustrated in the previous examples and these compounds were tested against wheat glume blotch and wheat leaf blotch using the protocols described herein.

Fungicidal Test for LEPTNO

Glume Blotch of Wheat (causal agent *Leptosphaeria nodorum*=Stagnospora nodorum; Bayer code LEPTNO): Wheat plants (variety Yuma) were grown from seed in a 50 pasteurized soil/50 percent soil-less mix until the seedlings had a fully expanded first leaf. Each pot contained 3-20 seedlings. These plants were sprayed until wet with the formulated test compound at a rate of 25 ppm. On the following day, the leaves were inoculated with an aqueous spore suspension of *Leptosphaeria nodorum* and the plants were kept in high humidity (one day in a dark dew chamber followed by four to seven days in a lighted dew chamber) to permit spores to germinate and infect the leaf. The plants were then transferred to a greenhouse until disease developed on untreated control plants.

Fungicidal Test for SEPTTR

Speckled Leaf Blotch of Wheat (*Mycosphaerella graminicola*=*Septoria tritici*; Bayer code SEPTTR): Wheat plants (variety Monon) were grown from seed in a greenhouse in 50% pasteurized soil/50% soil-less mix until the first true leaf was fully expanded, with 3-8 seedlings per pot. These plants were sprayed until wet with the formulated test compound at a rate of 25 ppm. On the following day, the leaves were inoculated with an aqueous spore suspension of *Septoria tritici* and the plants were kept in high humidity (one day in a dark dew chamber followed by four to seven days in a lighted dew chamber) to permit spores to germinate and infect the leaf. The plants were then transferred to a greenhouse until disease developed on untreated control plants.

TABLE 3

| Compound # | LEPTNO | SEPTTR |
|---|---|---|
| 80 | A | A |
| 81 | A | A |
| 88 | C | A |
| 92 | A | C |
| 93 | C | A |
| 109 | C | A |
| 110 | C | A |
| 111 | A | A |
| 112 | C | A |
| 114 | C | A |
| 118 | A | A |
| 119 | A | B |
| 128 | A | A |
| 187 | A | A |
| 234 | A | C |
| 236 | A | C |

LETPNO refers to in vitro control one day protectant at 25 ppm on wheat glume blotch
SEPTTR refers to in vitro control one day protectant at 25 ppm on wheat leaf blotch
In each case of TABLE 3 the rating scale is as follows:

| % Control | Rating |
|---|---|
| 50-100 | A |
| 26-49 | B |
| 1-25 | C |

We claim:

1. A compound of the Formula (I)

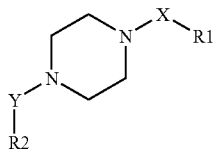

wherein
X and Y are each independently selected from the group consisting of a direct bond, alkyl, carbonyl, carbonylalkyl, carbonylalkylether, carboxylalkyl, alkylcarbonyl, alkylcarboxyl, and alkylether;
with the proviso that both X and Y cannot be a direct bond; and when
either X or Y is a direct bond, then the R1 or R2 associated with that bond is not phenyl or optionally substituted phenyl; and
R1 and R2 are each independently selected from the group consisting of:
alkyl;
aryl, optionally substituted with cyano, alkoxy, halogen, alkylhalo, alkoxyhalo, carboxylalkyl, carbonylalkyl, benzyloxy, nitro, benzoyl, phenyl, carboxamido, or heteroaryl;
heteroaryl, optionally substituted with aryl, heteroaryl, alkyl, halogen, alkylhalo, alkoxy, cycloalkyl or cyano;
cycloalkyl, optionally substituted with alkyl or halogen; and
a heterocyclic ring, optionally substituted with alkyl.

2. The compound of claim 1 wherein X and Y are each independently selected from the group consisting of a direct bond, alkyl, and carbonyl.

3. The compound of claim 2 wherein R1 and R2 are each independently selected from the group consisting of:
alkyl;
aryl, optionally substituted with cyano, alkoxy, halogen, alkylhalo, alkoxyhalo, carboxylalkyl, carbonylalkyl, benzyloxy, nitro, benzoyl, phenyl, carboxamido, or heteroaryl; and
heteroaryl, optionally substituted with aryl, heteroaryl, alkyl, halogen, alkylhalo, alkoxy, cycloalkyl or cyano.

4. An insecticidal or fungicidal composition comprising the compound of claim 1 and a phytologically acceptable carrier.

5. A method of controlling insects comprising applying to a locus where control is desired an insect-inactivating amount of a compound of claim 1.

6. A method for controlling fungal attack comprising applying to the soil, plant, roots, foliage, seed or locus of the fungus, or to a locus in which the infestation is to be controlled, a fungicidal effective amount of the compound of claim 1.

* * * * *